United States Patent
Nielsen et al.

(10) Patent No.: US 9,150,884 B2
(45) Date of Patent: Oct. 6, 2015

(54) MICROBIAL CONVERSION OF GLUCOSE TO STYRENE AND ITS DERIVATIVES

(75) Inventors: David Ross Nielsen, Tempe, AZ (US); Rebekah McKenna, Mesa, AZ (US)

(73) Assignee: Arizona Board of Regents, a Body Corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 172 days.

(21) Appl. No.: 14/003,713

(22) PCT Filed: Mar. 8, 2012

(86) PCT No.: PCT/US2012/028191
§ 371 (c)(1),
(2), (4) Date: Sep. 6, 2013

(87) PCT Pub. No.: WO2012/122333
PCT Pub. Date: Sep. 13, 2012

(65) Prior Publication Data
US 2014/0057325 A1     Feb. 27, 2014

Related U.S. Application Data

(60) Provisional application No. 61/450,200, filed on Mar. 8, 2011.

(51) Int. Cl.
*C12N 1/21* (2006.01)
*C12N 15/60* (2006.01)
*C12P 5/00* (2006.01)
*C12P 1/04* (2006.01)
*C12N 9/02* (2006.01)
*C12N 9/88* (2006.01)
*C12P 17/02* (2006.01)

(52) U.S. Cl.
CPC ............ *C12P 5/005* (2013.01); *C12N 9/0071* (2013.01); *C12N 9/88* (2013.01); *C12P 1/04* (2013.01); *C12P 17/02* (2013.01)

(58) Field of Classification Search
None
See application file for complete search history.

(56) References Cited

U.S. PATENT DOCUMENTS

| | | | |
|---|---|---|---|
| 3,660,235 | A | 5/1972 | Okumura et al. |
| 4,255,599 | A | 3/1981 | Wu et al. |
| 4,681,852 | A | 7/1987 | Tribe |
| 6,368,837 | B1 | 4/2002 | Gatenby et al. |
| 7,229,806 | B2 | 6/2007 | Ben-Bassat et al. |
| 7,303,900 | B2 | 12/2007 | Qi et al. |
| 7,368,267 | B2 | 5/2008 | Schmid et al. |
| 7,531,341 | B1 | 5/2009 | Vellard et al. |
| 2007/0259409 | A1 | 11/2007 | Wery |
| 2008/0220485 | A1 | 9/2008 | Lutje Spelberg et al. |
| 2010/0143996 | A1 | 6/2010 | Butler, III |

FOREIGN PATENT DOCUMENTS

| | | |
|---|---|---|
| EP | 0321488 B1 | 7/1993 |
| WO | 9307270 A1 | 4/1993 |
| WO | 9732023 A1 | 9/1997 |
| WO | 9811205 A2 | 3/1998 |
| WO | 2010119339 A2 | 10/2010 |

OTHER PUBLICATIONS

Cui et al., (2008). "Influence of amino acids, organic solvents and surfactants for phenylalanine ammonia lyase activity in recombinant *Escherichia coli*." Letters in Applied Microbiology 46: 631-635.
Fernandez et al., (2005). "Chemical composition of the essential oils from Turkish and Honduras Styrax." Flavour and Fragrance Journal 20: 70-73.
Goodey et al., (1982). "Genetic and biochemical analysis of the ability of Saccharomyces cerevisiae to decarboxylate cinnamic acids." Journal of general microbiology 128: 2615-2620.
Goodman, (2011). "A Plastic Pathway." Nature chemical biology 7: 576.
Hertweck et al., (2000). "A plant-like biosynthesis of benzoyl-CoA in the marine bacterium 'Streptomyces maritimus'." Tetrahedron 56: 9115-9120.
Ikeda et al., (1992). "Metabolic Engineering to Produce Tyrosine or Phenylalanine in a Tryptophan-Producing Corynebacterium glutamicum Strain." Appl Environ Microbiol 58(3): 781-785.
Larsson et al., (2001). "Effect of overexpression of Saccharomyces cerevisiae Pad1p on the resistance to phenylacrylic acids and lignocellulose hydrolysates under aerobic and oxygen-limited conditions." Applied Microbiology and Biotechnology 57: 167-174.
McKenna et al., (2011). "Styrene biosynthesis from glucose by engineered E. colo" Metabolic Engineering 13: 544-554.
Moffitt et al., (2007). "Discovery of two cyanobacterial phenylalanine ammonia lyases: Kinetic and structural characterization." Biochemistry 46(4): 1004-1012.
Mukai et al., (2010). "H. PAD1 and FDC1 are essential for the decarboxylation of phenylacrylic acids in Saccharomyces cerevisiae." Journal of Bioscience and Bioengineering 109(6): 564-569.
Panke et al., (2000). "Production of enantiopure styrene oxide by recombinant Escherichia coli synthesizing a two-component styrene monooxygenase." Biotechnology and Bioengineering 69(1): 91-100.
Panke et al., (2002). "Pilot-scale production of (S)-Styrene oxide from styrene by recombinant Escherichia coli synthesizing styrene monooxygenase." Biotechnology and Bioengineering 80(1): 33-41.
Qi et al., (2007). "Functional expression of prokaryotic and eukaryotic genes in Escherichia coli for conversion of glucose to p-hydroxystyrene." Metabolic engineering 9(3): 268-276.
Tischler et al., "StyA1 and StyA2B from Rhodococcus opacus 1CP: a Multifunctional Styrene Monooxygenase System." Journal of Bacteriology 192(19): 5220-5227.

(Continued)

*Primary Examiner* — Suzanne M Noakes
*Assistant Examiner* — Jae W Lee
(74) *Attorney, Agent, or Firm* — Quarles & Brady LLP; Gavin J. Milczarek-Desai

(57) ABSTRACT

A method for the in vivo production of styrene from renewable substrates using a recombinant microorganism is disclosed. Additionally, a method for the in vivo production of styrene oxide from renewable substrates using a recombinant microorganism is also disclosed. In both cases, the host cell expresses at least one gene encoding a polypeptide that possesses phenylalanine ammonia lyase activity in addition to at least one gene encoding a polypeptide that possesses trans-cinnamic acid decarboxylase activity. In the case of styrene oxide, the host cell must additionally express at least one gene encoding a polypeptide that possesses styrene monooxygenase activity.

16 Claims, 5 Drawing Sheets

(56) References Cited

OTHER PUBLICATIONS

Verhoef et al., (2007). "Bioproduction of p-hydroxybenzoate from renewable feedstock by solvent-tolerant Pseudomonas putida S12." Journal of biotechnology 132(1): 49-56.

Verhoef et al., (2009). "Bioproduction of p-hydroxystyrene from glucose by the solvent-tolerant bacterium Pseudomonas putida S12 in a two-phase water-decanol fermentation." Appl Environ Microbiol 75(4): 931-936.

Wierckx et al., (2005). "Engineering of solvent-tolerant Pseudomonas putida S12 for bioproduction of phenol from glucose." Appl Environ Microbiol 71(12): 8221-8227.

Xiang et al., (2005). "Biochemical characterization of a prokaryotic phenylalanine ammonia lyase." Journal of Bacteriology 187(12): 4286-4289 (2005).

p-coumaric acid trans-cinnamic acid

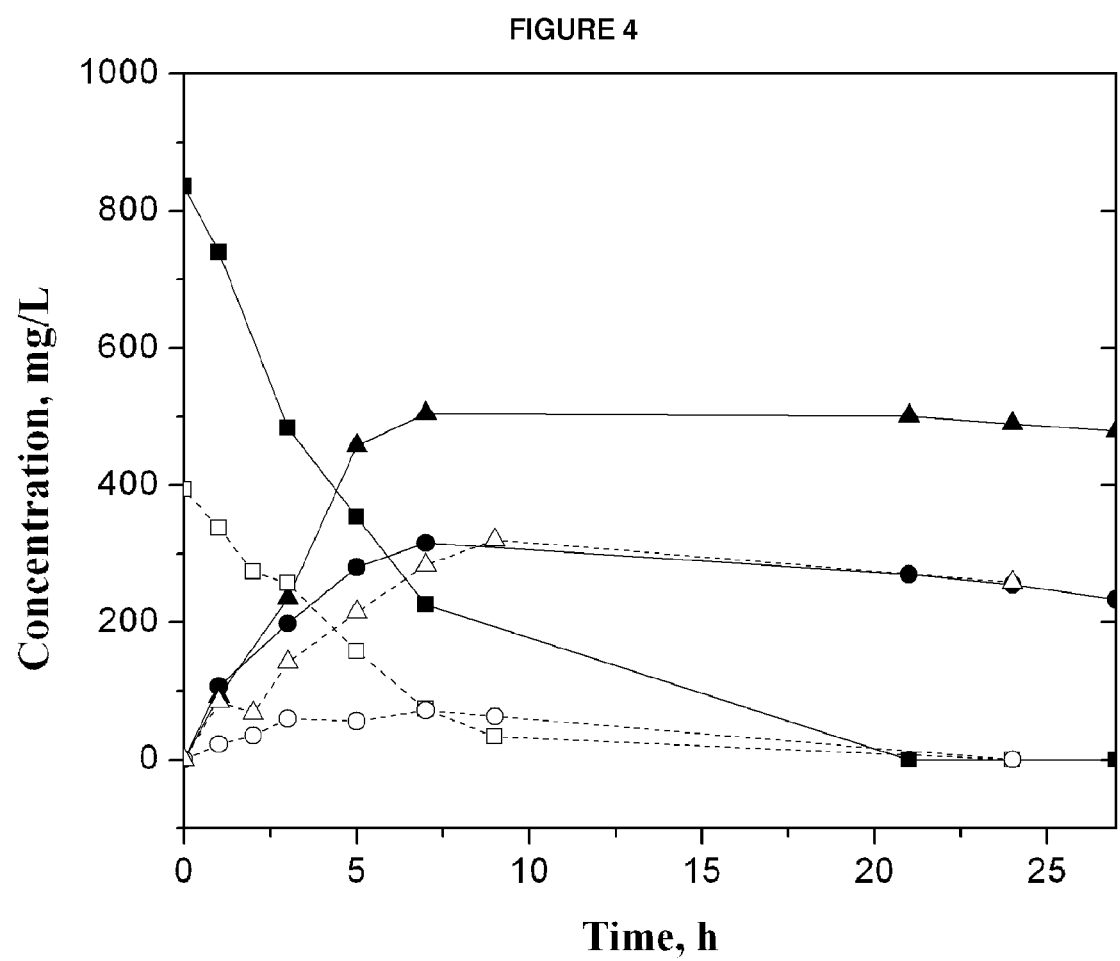

US 9,150,884 B2

MICROBIAL CONVERSION OF GLUCOSE TO STYRENE AND ITS DERIVATIVES

RELATED APPLICATIONS

This application is a 371 application of PCT/US2012/028191 filed Mar. 8, 2012, which claims the benefit of priority of U.S. Provisional Application No. 61/450,200, which was filed on Mar. 8, 2011. The entire text of the aforementioned applications is incorporated herein by reference.

FEDERALLY SPONSORED RESEARCH OR DEVELOPMENT

[Not Applicable]

FIELD OF THE INVENTION

This invention relates to the fields of molecular biology, microbiology, and biotechnology. More specifically, the present invention relates to a method of producing styrene and styrene oxide from simple renewable substrates such as glucose.

BACKGROUND OF THE INVENTION

Styrene is a useful and versatile monomer for the production of numerous polymers and co-polymers, which accounts for 60% of its total global use[1]. Styrene is most commonly yielded by the chemocatalytic dehydrogenation of petroleum-derived ethylbenzene (U.S. Pat. No. 4,255,599), a process requiring over 3 metric tons of steam per metric ton of styrene produced. This exorbitant requirement renders styrene production as the most energy-intensive among commodity chemical production routes, consuming nearly 200 trillion BTU of steam for its domestic annual production alone[2]. In 2006, over 6 million metric tons of styrene were produced by U.S. manufacturers alone, representing a market that is currently valued at nearly $28 billion and projected to grow by 4.3% per year through at least 2010[1]. A more sustainable and inexpensive approach would involve the engineering of microorganisms that possess the unique ability to synthesize styrene at high levels directly from renewable resources. Presently, however, an inexpensive and sustainable source of styrene has not yet been developed.

A variety of additional novel synthetic routes have recently been engineered in microorganisms for the production, from substrates such as glucose, of a number of other useful monoaromatic compounds with structural similarity to styrene. For example, a biosynthetic pathway for the production of p-hydroxystyrene (pHS; a monomer used in polymer synthesis) from renewable sugars has been reported using *E. coli*[4] or *P. putida*[5] as the engineered host platform. Meanwhile, both phenol (a precursor and monomer for phenolic resins)[6] and p-hydroxybenzoate (a precursor to parabens, which are used as preservatives)[7] have also been synthesized as individual products from glucose by engineered strains of *P. putida*. These studies further illustrate how, through metabolic engineering strategies, microbial biocatalysts can be developed for the sustainable biosynthesis of a variety of important commodity chemicals of monoaromatic nature from renewable resources. Each of the above non-natural metabolites were derived using L-tyrosine (or its immediate precursor, 4-hydroxyphenylpyruvate) as a precursor (thereby making them all phenolics). There are, however, no previously reported studies on the production of styrene from renewable resources (for example, carbohydrates such as glucose) by either naturally-occurring or recombinant microorganisms.

L-Phenylalanine is a naturally-occurring, proteinogenic amino acid that is ubiquitous among most all living organisms. Although its natural biosynthesis is often tightly regulated, its overproduction on fermentable sugars has been engineered in several microorganisms, and most notably in *Escherichia coli* (U.S. Pat. No. 4,681,852) and *Corynebacterium glutamicum* (U.S. Pat. No. 3,660,235).

Phenylalanine ammonia lyase (PAL) activity has been reported in a number of marine bacteria, including *Anabaena variabilis, Nostoc punctiforme*, and *Streptomyces maritimus*, and the genes have been identified[8-10]. In addition, the yeast *Rhodotoruloides glutinis* has been well-studied with regards to its phenylalanine ammonia lyase (PAL) activity, however, the identified and characterized gene product is less specific in that it also functions as a tyrosine ammonia lyase (TAL)[4,11]. It is further known that the yeast *Saccharomyces cerevisiae* is capable of synthesizing styrene when supplied with exogenous trans-cinnamic acid (Calif.)[12]. That is to say, the yeast *Saccharomyces cerevisiae* is known to naturally display trans-cinnamic acid decarboxylase (CADC) activity. It has been further demonstrated that this native enzymatic ability has an essential dependence on the combined expression of the enzymes encoded by the genes PAD1 and FDC1[13].

In light of the foregoing, it would be an advancement in the current state of the art to provide a method by which styrene could be produced from inexpensive and sustainable resources such as carbohydrates or sugars. It would be particularly advantageous if the method produced a high level of styrene at high substrate yields and with a limited diversity and quantity of by-products. The development of such a method will require the ability to manipulate and assemble the appropriate genetic machinery responsible for the conversion of carbohydrates such as glucose to CA, and CA to styrene. It would be exceptionally advantageous if these conversions could all be achieved within a single host cell.

The above mentioned biological and chemical systems provide both examples of a number of potentially useful genetic elements, as well as a number of pathways that may be useful in the biological production of styrene, however the efficient biological production of styrene has not been achieved. Therefore, the problem to be overcome is to design and develop a method for the efficient production of styrene by a biological source using inexpensive substrates as the carbon source. The applicants have solved the stated problem by engineering a microbial host to produce styrene by expression of foreign genes which encode phenylalanine ammonia lyase (PAL) and trans-cinnamic acid decarboxylase (CADC).

Furthermore, (S)-styrene oxide may be produced by the enzymatic oxidation of styrene by the additional co-expression of a gene encoding a polypeptide with styrene monooxygenase (SMO) activity. Epoxides are desirable compounds due to their versatile nature as chemical building blocks. More specifically, (S)-styrene oxide is a functional building block that is used as a precursor to a variety of pharmaceutical compounds including levamisole and some analgesics[14]. Enzymatic reactions, as opposed to chemical processes, have the unique ability to yield enantiomerically pure products. The styrene oxygenase activity of several *Pseudomonas* sp. has been identified as the two-component styrene monooxygenase encoded by styAB[14]. Activity has also been reported for the two-component flavoprotein monooxygenase encoded by styA2B present in *Rhodococcus opacus* 1CP[15].

BRIEF SUMMARY OF THE INVENTION

The present invention comprises an in vivo method for the production of styrene via a recombinant host cell expressing at least one gene encoding a polypeptide having phenylalanine ammonia lyase (PAL) activity to convert endogenously-synthesized L-phenylalanine to trans-cinnamic acid in combination with at least one gene encoding a polypeptide having trans-cinnamate decarboxylase (CADC) activity to then subsequently convert trans-cinnamic acid to styrene. This reaction scheme is illustrated in FIG. 1A. The present invention also comprises an in vivo method for the production of styrene oxide by further engineering said recombinant host cell to additionally co-express at least one gene encoding a polypeptide that displays styrene monooxygenase (SMO) activity. This reaction scheme is illustrated in FIG. 1B. This invention provides an inexpensive and sustainable biological route for the conversion of renewable substrates to styrene. Styrene is useful, for example, for the synthesis of numerous polymers and co-polymers. This invention additionally provides an inexpensive and sustainable biological route for the conversion of renewable substrates to (S)-styrene oxide. (S)-Styrene oxide is a molecular building block used in the production of a variety of pharmaceuticals.

Accordingly, the present invention provides a method for the production of styrene comprising:
  i) contacting a recombinant host cell with a fermentable carbon source, said recombinant host comprising:
    a) at least one gene encoding a polypeptide having phenylalanine ammonia lyase activity; and
    b) at least one gene encoding a polypeptide having trans-cinnamate decarboxylase activity
  ii) growing said recombinant cell for a time sufficient to produce styrene; and
  iii) optionally recovering said styrene.

Alternatively, the invention provides a method for the production of styrene comprising:
  i) contacting a recombinant host cell with a fermentable carbon source, said recombinant host comprising:
    a) at least one gene encoding a polypeptide having phenylalanine ammonia lyase activity; and
    b) at least one gene encoding a polypeptide having phenylacrylic acid decarboxylase activity
  ii) growing said recombinant cell for a time sufficient to produce styrene; and
  iii) optionally recovering said styrene.

Alternatively, the invention provides a method for the production of styrene comprising:
  i) contacting a recombinant host cell with a fermentable carbon source, said recombinant host comprising:
    a) at least one gene encoding a polypeptide having phenylalanine ammonia lyase activity; and
    b) at least one gene encoding a polypeptide having ferulic acid decarboxylase activity
  ii) growing said recombinant cell for a time sufficient to produce styrene; and
  iii) optionally recovering said styrene.

Additionally, the present invention also provides a method for the production of styrene oxide comprising:
  i) contacting a recombinant host cell with a fermentable carbon source, said recombinant host comprising:
    a) at least one gene encoding a polypeptide having phenylalanine ammonia lyase activity; and
    b) at least one gene encoding a polypeptide having trans-cinnamate decarboxylase activity
    c) at least one gene encoding a polypeptide having styrene monooxygenase activity
  ii) growing said recombinant cell for a time sufficient to produce styrene oxide; and
  iii) optionally recovering said styrene oxide.

Alternatively, the present invention also provides a method for the production of styrene oxide comprising:
  i) contacting a recombinant host cell with a fermentable carbon source, said recombinant host comprising:
    a) at least one gene encoding a polypeptide having phenylalanine ammonia lyase activity; and
    b) at least one gene encoding a polypeptide having phenylacrylic acid decarboxylase activity
    c) at least one gene encoding a polypeptide having styrene monooxygenase activity
  ii) growing said recombinant cell for a time sufficient to produce styrene oxide; and
  iii) optionally recovering said styrene oxide.

Alternatively, the present invention also provides a method for the production of styrene oxide comprising:
  i) contacting a recombinant host cell with a fermentable carbon source, said recombinant host comprising:
    a) at least one gene encoding a polypeptide having phenylalanine ammonia lyase activity; and
    b) at least one gene encoding a polypeptide having ferulic acid decarboxylase activity
    c) at least one gene encoding a polypeptide having styrene monooxygenase activity
  ii) growing said recombinant cell for a time sufficient to produce styrene oxide; and
  iii) optionally recovering said styrene oxide.

Additionally, the invention provides a recombinant host cell comprising:
  a) a gene encoding a polypeptide having phenylalanine ammonia lyase activity; and
  b) a gene encoding a polypeptide having trans-cinnamate decarboxylase activity Additionally, the invention provides a recombinant host cell comprising:
  a) a gene encoding a polypeptide having phenylalanine ammonia lyase activity; and
  b) a gene encoding a polypeptide having phenylacrylic acid decarboxylase activity Additionally, the invention provides a recombinant host cell comprising:
  a) a gene encoding a polypeptide having phenylalanine ammonia lyase activity; and
  b) a gene encoding a polypeptide having ferulic acid decarboxylase activity Additionally, the invention provides a recombinant host cell comprising:
  a) a gene encoding a polypeptide having phenylalanine ammonia lyase activity; and
  b) a gene encoding a polypeptide having trans-cinnamate decarboxylase activity
  c) a gene encoding a polypeptide having styrene monooxygenase activity Additionally, the invention provides a recombinant host cell comprising:
  a) a gene encoding a polypeptide having phenylalanine ammonia lyase activity; and
  b) a gene encoding a polypeptide having phenylacrylic acid decarboxylase activity
  c) a gene encoding a polypeptide having styrene monooxygenase activity Additionally, the invention provides a recombinant host cell comprising:
  a) a gene encoding a polypeptide having phenylalanine ammonia lyase activity; and
  b) a gene encoding a polypeptide having ferulic acid decarboxylase activity c) a gene encoding a polypeptide having styrene monooxygenase activity.

BRIEF DESCRIPTION OF SEVERAL VIEWS OF THE DRAWINGS

FIG. 4. Whole cell production of styrene (triangle) from trans-cinnamic acid (circle) after the addition of L-phenylalanine (square) by *E. coli* NST74 pSpal2At pTfdc1Sc.

BRIEF DESCRIPTION OF THE SEQUENCE LISTING

Figure 1:
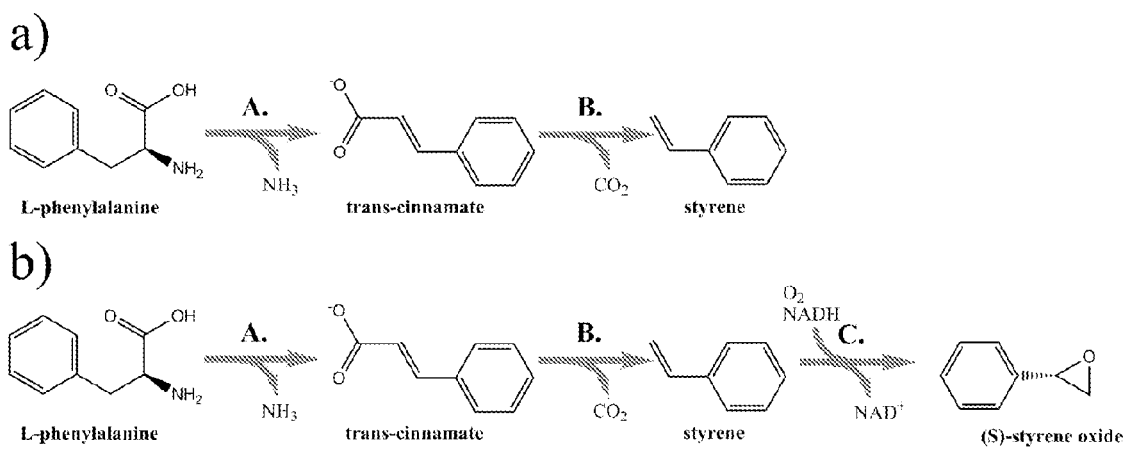
FIG. 1. A) Enzymatic pathway to convert the precursor L-phenylalanine to the product styrene via the intermediate trans-cinnamate. The two-step pathway from L-phenylalanine is achieved by the co-expression of one or more genes which encoded phenylalanine ammonia lyase (PAL) activity (A), and one or more genes which encoded trans-cinnamic acid decarboxylase (CADC) activity (B). B) Enzymatic pathway to convert the precursor L-phenylalanine to the product (S)-styrene oxide via the intermediates trans-cinnamate and styrene. The three-step pathway from L-phenylalanine is achieved by the co-expression of one or more genes which encode phenylalanine ammonia lyase (PAL) activity (A), one or more genes which encode trans-cinnamic acid decarboxylase (CADC) activity (B), and one or more genes which encode styrene monooxygenase (SMO) activity (B).

SEQ ID NO:1 is the nucleotide sequence of a gene from *A. variabilis* encoding a phenylalanine ammonia lyase.
SEQ ID NO:2 is the nucleotide sequence of a gene from *N. punctiforme* encoding a phenylalanine ammonia lyase.
SEQ ID NO:3 is the nucleotide sequence of a gene from *S. maritimus* encoding a phenylalanine ammonia lyase.
SEQ ID NO:4 is the nucleotide sequence of a gene from *A. thaliana* encoding a phenylalanine ammonia lyase.
SEQ ID NO:5 is the nucleotide sequence of a gene from *A. thaliana* encoding a phenylalanine ammonia lyase.
SEQ ID NO:6 is the nucleotide sequence of a gene from *P. putida* encoding a styrene monooxygenase.
SEQ ID NO:7 is the nucleotide sequence of a gene from *R. opacus* encoding a styrene monooxygenase
SEQ ID NO:8 is the nucleotide sequence of a gene from *L. plantarum* encoding a phenylacrylic acid decarboxylase.
SEQ ID NO:9 is the nucleotide sequence of a gene from *B. subtilis* encoding a phenylacrylic acid decarboxylase.
SEQ ID NO:10 is the nucleotide sequence of a gene from *S. cerevisiae* encoding a phenylacrylic acid decarboxylase.
SEQ ID NO:11 is the nucleotide sequence of a gene from *S. cerevisiae* encoding a ferulic acid decarboxylase.
SEQ ID NO:12 is a primer used to amplify pal from *A. variabilis*.
SEQ ID NO:13 is a primer used to amplify pal from *A. variabilis*.
SEQ ID NO:14 is a primer used to amplify pal from *N. punctiforme*.
SEQ ID NO:15 is a primer used to amplify pal from *N. punctiforme*.
SEQ ID NO:16 is a primer used to amplify encP from *S. maritimus*.
SEQ ID NO:17 is a primer used to amplify encP from *S. maritimus*.
SEQ ID NO:18 is a primer used to amplify pdc from *L. plantarum*.
SEQ ID NO:19 is a primer used to amplify pdc from *L. plantarum*.
SEQ ID NO:20 is a primer used to amplify padC from *B. subtilis*.
SEQ ID NO:21 is a primer used to amplify padC from *B. subtilis*.
SEQ ID NO:22 is a primer used to amplify PAD1 from *S. cerevisiae*.
SEQ ID NO:23 is a primer used to amplify PAD1 from *S. cerevisiae*.
SEQ ID NO:24 is a primer used to amplify FDC1 from *S. cerevisiae*.
SEQ ID NO:25 is a primer used to amplify FDC1 from *S. cerevisiae*.
SEQ ID NO:26 is a primer used to amplify PAL1 from *A. thaliana*.
SEQ ID NO:27 is a primer used to amplify PAL1 from *A. thaliana*.
SEQ ID NO:28 is a primer used to amplify PAL2 from *A. thaliana*.
SEQ ID NO:29 is a primer used to amplify PAL2 from *A. thaliana*.
SEQ ID NO:30 is a primer used to amplify styAB from *P. putida*.
SEQ ID NO:31 is a primer used to amplify styAB from *P. putida*.
SEQ ID NO:32 is a primer used to amplify styA2B from *R. opacus*.
SEQ ID NO:33 is a primer used to amplify styA2B from *R. opacus*.

DETAILED DESCRIPTION OF THE INVENTION

The following abbreviations and definitions will be used for the interpretation and specification of the claims.
"Phenylalanine ammonia lyase" is abbreviated PAL.
"Tyrosine ammonia lyase" is abbreviated TAL.
"Phenylacrylic acid decarboxylase" is abbreviated PADC.
"trans-Cinnamic acid decarboxylase" is abbreviated CADC.

"Ferulic acid decarboxylase" is abbreviated FADC.

"Styrene monooxygenase" is abbreviated SMO.

As used herein, the terms "L-phenylalanine", and "phenylalanine" are used interchangeably.

As used herein, the terms "trans-cinnamic acid", "cinnamic acid", trans-cinnamate", and "cinnamate" are used interchangeably and are abbreviated CA.

As used herein, the terms "ferulic acid" and "ferulate" are used interchangeably.

As used herein, the terms "(S)-styrene monooxygenase" and "styrene monooxygenase" are used interchangeably.

The term "PAL activity" refers to the ability of a protein to catalyze the direct conversion of phenylalanine to CA.

The term "CADC activity" refers to the ability of a protein to catalyze the direct conversion of CA to styrene.

The term "SMO activity" refers to the ability of a protein to catalyze the direct conversion of styrene to (S)-styrene monooxygenase.

The term "phenylalanine over-producing strain" refers to a microbial strain that produces endogenous levels of phenylalanine that are significantly higher than those demonstrated by the wild-type of that strain. Specific examples of an E. coli phenylalanine over-producing strains are NST74 and NST37 (U.S. Pat. No. 4,681,852). Meanwhile, still others may include specific strains of Corynebacterium glutamicum[16].

The term "fermentable carbon substrate" refers to a carbon source capable of being metabolized by the host organisms of the present invention and particularly carbon sources selected from the group consisting of monosaccharides, oligosaccharides, polysaccharides, organic acids, glycerol, and one-carbon substrates or mixtures thereof.

The term "host" refers to a suitable cell line such as a strain of bacteria, for example, into which genes can be transferred to impart desired genetic attributes and functions.

The term "$OD_{600}$" refers to the measurement of optical density at 600 nm, a standard metric of cell growth used by those familiar in the art.

The term "gene" refers to a nucleic acid fragment that expresses a specific protein, including regulatory sequences preceding (5' non-coding sequences) and following (3' non-coding sequences) and the coding sequence. "Native gene" or "wild type gene" refers to a gene as found in nature with its own regulatory sequences. "Endogenous gene" refers to a native gene in its natural location in the genome of an organism. "Foreign gene" refers to a gene not normally found in the host organism but that is introduced into the host organism by gene transfer. Foreign genes can comprise native genes inserted into a non-native organism, or chimeric genes.

The term "expression", as used herein, refers to the transcription and stable accumulation of sense (mRNA) or antisense RNA derived from the nucleic acid fragment used in this invention. Expression may also refer to the translation of the mRNA into a polypeptide. "Overexpression" refers to the production of a gene product in a transgenic organism that exceeds levels of production in the wild-type host or native organisms.

"RNA transcript" refers to the product resulting from RNA polymerase-catalyzed transcription of gene or other a DNA sequence. "Messenger RNA (mRNA)" refers to the RNA that is without introns and can be translated into a protein by the cell. "cDNA" refers to double-stranded DNA that is complimentary to and derived from mRNA. "Sense" RNA refers to RNA transcript that includes the mRNA and so can be translated into protein by the cell.

"Transformation" refers to the transfer of a nucleic acid fragment into the genome of the host organism, resulting in genetically-stable inheritance. Host organisms containing the transformed nucleic acid fragments are referred to as "transgenic" or "recombinant" or "transformed" organisms.

The terms "plasmid" and "vector" refer to an extra chromosomal genetic element often carrying genes which are not part of host native genome nor the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Genes

The key enzymatic activities used in the present invention are encoded by a number of genes known in the art. The principal enzyme activities include phenylalanine ammonia lyase (PAL) and trans-cinnamic acid decarboxylase (CADC). These activities may also be displayed by enzymes whose principal natural substrates are not phenylalanine or trans-cinnamic acid, respectively, but also those which have the natural capacity to utilize these substrates or which can be engineered to display these activities.

Phenylalanine ammonia lyase (PAL) and trans-cinnamic acid decarboxylase (CADC) activities Genes encoding PAL activity are known in the art and several have been sequenced from both microbial and plant origin (see, for example, EP 321488 [R. toruoides]; WO 9811205 [Eucalyptis grandis and Pinus radiata]; WO 9732023 [Petunia]; JP 05153978 [Pisum sativum]; WO 9307270 [potato, rice]; NM_129260.2 GI:30687012 and NM_115186.3 GI:42565889 [Arabdiposis thaliana]). The sequence of PAL encoding genes are available (for example, see GenBank AJ010143 and X75967). Where expression of a wild type PAL in a recombinant host is desired, the wild type gene may be obtained from any source including, but not limited to, yeasts such as Rhodotorula sp., Rhodosporidium sp., and Sporobolomyces sp.; bacteria such as Streptomyces sp., Anabaena sp., and Nostoc sp.; and plants such as pea, potato, rice, eucalyptus, pine, corn, petunia, arabidopsis, tobacco, and parsley. It is preferred, but not necessary, that enzymes should strictly display PAL activity and not TAL activity as well.

Genes which purportedly encode trans-cinnamic acid decarboxylase (CADC) activity have been identified in the literature. In addition, enzymes which have been classified as phenylacrylic acid decarboxylase (PADC) or ferulic acid decarboxylase (FADC) may also display the necessary CADC activity. Genes encoding PADC activity, for example, have been isolated from the bacteria Lactobacillus plantarum (AAC45282.1 GI: 1762616), Lactococcus lactis (NP_268087.1 GI:15673912), and Bacillus subtilis (AF017117.1 GI:2394281). The PADC encoding genes from Lactobacillus plantarum and Bacillus subtilis are listed herein as SEQ ID NO:8 and SEQ ID NO:9, respectively. Furthermore, CADC activity has been reported in the yeast Saccharomyces cerevisiae and it was shown that the display of this native activity required that the genes PAD1 (L09263.1 GI:393284) and FDC1 (NP_010828.1 GI:6320748) both be present and undisturbed in the genome[13]. Genomic disruption of either PAD1 or FDC1, whose sequences are provided as SEQ ID NO:10 and SEQ ID NO:11, respectively, resulted in the loss of CADC activity upon exogenously supplied trans-cinnamic acid[13]. However, considering the structural similarity between ferulic acid and trans-cinnamic acid, we anticipated that enzymes which are known to display ferulic acid decarboxylase (FADC) activity, such as the polypeptide encoded by FDC1 of *S. cerevisiae*, may also display trans-cinnamic acid decarboxylase (CADC) activity as well.

It will be appreciated that the present invention is not limited to the genes encoding polypeptides having the specific activities mentioned above, but will encompass any suitable homologs of such genes that may be obtained by standard methods. Methods of obtaining homologs to these genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR)).

For example, genes encoding homologs of the polypeptides that alone or in combination have the above mentioned activities could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art. Moreover, the entire sequences can be used directly to synthesize DNA probes by methods known to those skilled in the art, such as random primers DNA labeling, nick translation, or end-labeling techniques or RNA probes using available in vitro transcription systems. In addition, specific primers can be designed and used to amplify a part of or full length of the instant sequences. The resulting amplification products can be labeled directly during amplification reactions or labeled after amplification reactions, and used as probes to isolate full-length cDNA or genomic fragments under conditions of appropriate stringency.

Microbial Production Hosts

The production organisms of the present invention will include any organism capable of expressing the genes required for styrene production. Typically, the production organism will be restricted to microorganisms or plants. Microorganisms useful in the present invention include, but are not limited to enteric bacteria (*Escherichia* and *Salmonella*, for example) as well as *Bacillus*, *Acinetobacter*, Actinomycetes such as *Streptomyces*, *Corynebacterium*, Methanotrophs such as *Methylosinus*, *Methylomonas*, *Rhodococcus* and *Pseudomonas*; Cyanobacteria, such as *Rhodobacter* and *Synechocystis*; yeasts, such as *Saccharomyces*, *Zygosaccharomyces*, *Kluyveromyces*, *Candida*, *Hansenula*, *Debaryomyces*, *Mucor*, *Pichia*, and *Torulopsis*; and filamentous fungi such as *Aspergillus* and *Arthrobotrys*, and algae, for example. The genes encoding polypeptides with the PAL and CADC activities used in the present invention may be produced or over-expressed in these and other microbial hosts to prepare large quantities of styrene.

Although any of the above mentioned microorganisms would be useful for the production of styrene, preferred strains would be those that either natively or have been engineered to over-produce phenylalanine. Phenylalanine over-producing strains are known and include, but are not limited to, *Escherichia* sp., *Corynebacterium* sp., *Microbacterium* sp., *Arthrobacter* sp., *Pseudomonas* sp., and *Brevibacteria* sp. Particularly useful phenylalanine over-producing strains include, but are not limited to, *Microbacterium ammoniaphilum* ATCC 10155, *Corynebacterium lillium* NRRL-B-2243, *Corynebacterium glutamicum* ATCC 21674, *E. coli* NST74, *E. coli* NST37, and *Arthrobacter citreus* ATCC 11624. A recombinant host may be constructed from a suitable phenylalanine over-producing strain such that it expresses at least one gene encoding a polypeptide having PAL and at least one gene encoding a polypeptide having CADC activity.

Microbial expression systems and expression vectors containing regulatory sequences that direct high level expression of foreign proteins and overexpression of native proteins are well known to those skilled in the art. Any of these could be used to construct chimeric genes for the production of styrene. These chimeric genes could then be introduced into appropriate microorganisms via transformation to allow for expression of high levels of the enzymes.

DESCRIPTION OF THE PREFERRED EMBODIMENTS

The method of production defined in this invention involves the incorporation of genes encoding polypeptides displaying PAL and CADC activities into a single host organism and the use of those organisms to convert renewable resources, including fermentable carbons sources such as glucose, for example, to styrene. This invention relies upon the identification of genes encoding PAL and CADC activities and, preferably, those genes which when expressed in a recombinant host organism can display such activities. Candidate genes encoding PAL homologs were selected from the open literature and included pal from *Anabaena variabilis*, pal from *Nostoc punctiforme*, encP from *Streptomyces maritimus*, and PAL1 and PAL2 from *Arabidopsis thaliana*. Each gene was amplified from genomic DNA samples via PCR, cloned individually into the expression vector pSTV28. This resulted in the generation of plasmids pSpalAv, pSpalNp, pSencPSm, pSpal1At, and pSpal2At, respectively. Each plasmid was then individually transformed into *E. coli*.

Candidate genes encoding CADC homologs were selected from the open literature and included pdc from *Lactobacillus plantarum*, padC from *Bacillus subtilis*, PAD1 from *Saccharomyces cerevisiae*, and FDC1 from *Saccharomyces cerevisiae*. Each gene was amplified from genomic DNA samples via PCR, cloned individually into the expression vector pTrc99a. This resulted in the generation of plasmids pTpdcLp, pTpadcBs, pTpad1Sc, and pTfdc1Sc, respectively. In addition, FDC1 from *Saccharomyces cerevisiae* was also cloned into pTrc99a together with PAD1 as part of a synthetically-assembled, polycistronic operon. This resulted in the generation of plasmids pTpad1Sc-fdc1Sc. Each plasmid was then individually transformed into *E. coli*.

Figure 2:
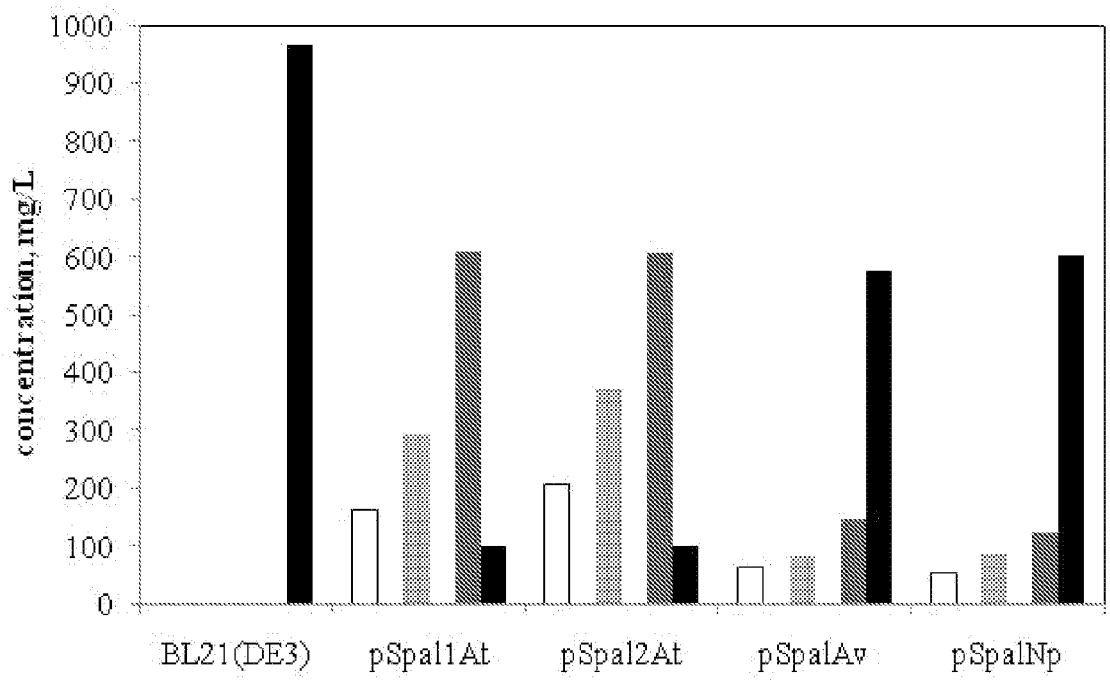
FIG. 2. Phenylalanine ammonia lyase activity from candidate genes cloned from *A. thaliana*, *A. variabilis*, and *N. punctiforme* in recombinant *E. coli* BL21(DE3) whole cells. 50 ml cultures were grown for 8 h (induced with 0.2 mM IPTG after 1.5 h), centrifuged to obtain a pellet and resuspended in 10 ml pH7 PBS buffer. The conversion of 1 g/L L-phenylalanine (black) to trans-cinnamic acid after 1 h (white), 2 h (light gray), and 3 h (dark gray). Note that no activity was observed in the control (*E. coli* BL21(DE3)).
Figure 3A:
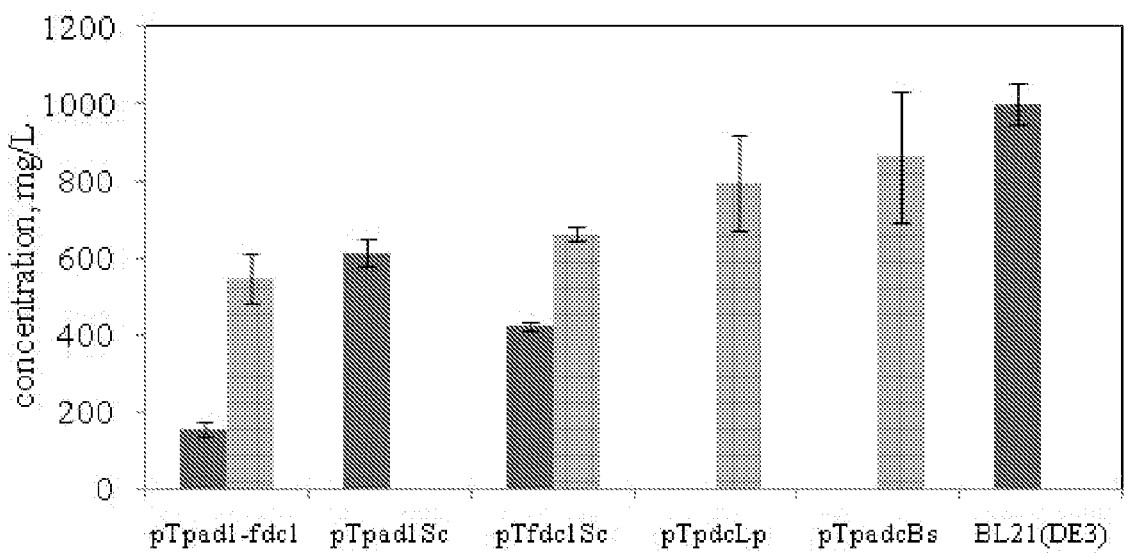
FIG. 3. trans-Cinnamic acid decarboxylase activity from candidate genes cloned from *S. cerevisiae*, *L. plantarum*, and *B. subtilis* in recombinant *E. coli* BL21(DE3) whole cells. 50 ml cultures were grown for 8 h (induced with 0.2 mM IPTG after 1.5 h), centrifuged to obtain a pellet and resuspended in 10 ml pH7 PBS buffer. The conversion of A) 1 g/L p-coumaric acid (dark gray) to p-hydroxystyrene (light gray) and B) 1 g/L trans-cinnamic acid (dark gray) to styrene (light gray) after 12 h. Not that no activity is observed in the control (*E. coli* BL21(DE3)).
Figure 3B:
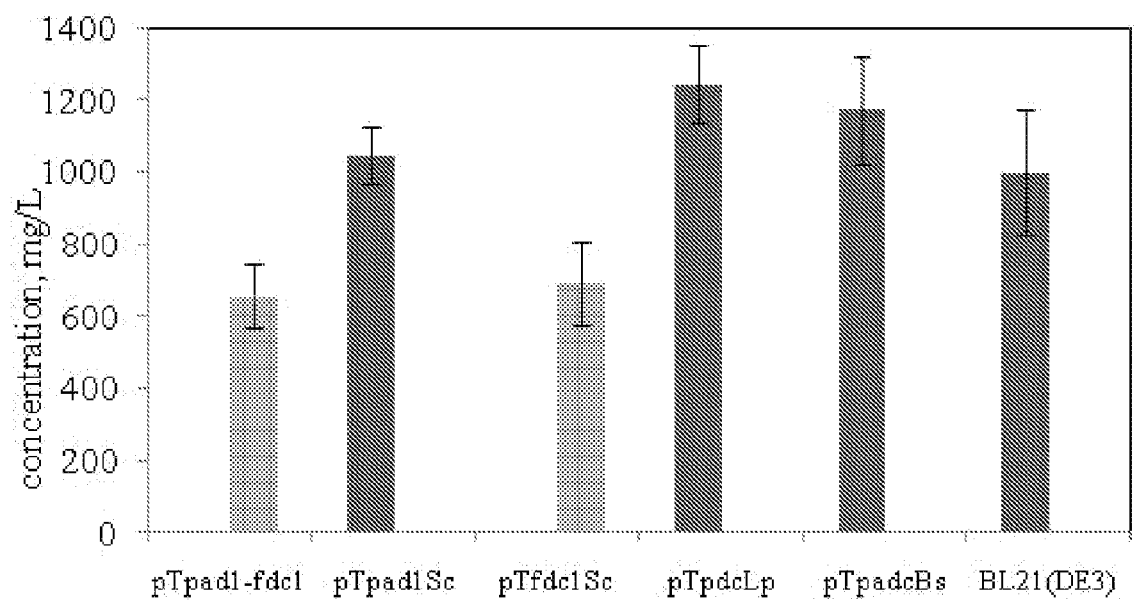

Screening assays were performed on both whole cells and cell extracts. PAL activity was investigated via the conversion of exogenous phenylalanine to CA, whereas CADC activity was investigated via the conversion of exogenous CA to styrene. As seen in FIG. 2 and Table 1, PAL activity was confirmed in recombinant *E. coli* according to both whole cell and cell extract assays in strains expressing pal from *Nostoc punctiforme*, pal from *Anabaena variabilis*, PAL1 from *Arabidopsis thaliana*, or preferably PAL2 from *Arabidopsis thaliana*. As seen in FIG. 3, CADC activity was confirmed in recombinant *E. coli* according to whole cell assays in strains expressing FDC1 from *Saccharomyces cerevisiae*.

EXAMPLES

The present invention is further defined in the following Examples. It should be understood that these Examples, while indicating preferred embodiments of the invention, are given by way of illustration only. From the above discussion and these following Examples, one skilled in the art can ascertain the essential characteristics of this invention, and without departing from the spirit and scope thereof, can make various changes and modifications of the invention to adapt it to various uses and conditions.

Procedures required for PCR amplification, DNA modifications by endo- and exonucleases for generating desired ends for cloning of DNA, ligation, and bacterial transformation are well known in the art. The standard molecular biology techniques used herein are well-known in the art and described by Sambook, J., Fritsch, E. F., and Maniatis, T., *Molecular Cloning: A Laboratory Manual*, 2$^{nd}$ ed.; Cold Spring Harbor Laboratory: Cold Spring Harbor, N.Y., 1989.

Materials and methods suitable for the maintenance and growth of microbial cultures are well known in the art. Methods and techniques suitable for use in the following set of Examples may be found for example, as described in *Manual of Methods for General Bacteriology*; Gerhardt, P., Murray, R. G. F., Costilow, R. N., Nester, E. W., Wood, W. A., Krieg, N. R., and Phillips, G. B., Eds., American Society for Microbiology: Washington, D.C., 1994. All reagents used in the Examples were purchased from Sigma Aldrich (St. Louis, Mo.). Restriction enzymes, polymerases, and ligase were purchased from New England Biolabs (Ipswich, Mass.). Nutrients and chemicals used for the growth and maintenance of cells were purchased from DIFCO Laboratories (Detroit, Mich.).

General Methods

PCR reactions were performed using a BioRad iCycler system with Phusion DNA Polymerase (Finnzymes, Espoo, Finland). Custom DNA oligonucleotide primers were synthesized by and purchased from Integrated DNA Technologies (Coralville, Iowa). PCR cycling and reaction conditions were standardized according to manufacturer instructions.

An HPLC assay was developed to simultaneously separate and measure aqueous levels of phenylalanine, CA, and styrene in microbial cultures. For a typical assay, 1 mL culture was removed from shake flask culture and centrifuged to pellet cells. 0.75 mL of supernatant was then transferred to a sealed HPLC vial. A Hewlett Packard 1100 series HPLC system with an auto sampler and a diode array UV/Vis detector with a reverse-phase Hypersil Gold SBC18 column (4.6 mm×150 mm; Thermo Fisher, USA) was used to achieve separation and detection of the species. 5 microliters of sample was injected for analysis according to the following methodology. A total flow rate of 1.0 ml/min and column temperature of 45° C. were held constant throughout. The column was eluted with solvent A containing double-distilled water and solvent B containing methanol plus 0.1% trifluoroacetic acid (TFA). The eluent initially consisted of 95% solvent A and 5% solvent B and then, over the course of the first 8 min, a linear gradient was applied to eventually reach 80% solvent B and 20% solvent A. These conditions were then held for 2 min before a linear gradient returning to the final conditions of 95% solvent A and 5% solvent B was applied over the course of 4 min. The UV detector was used to monitor the eluent at 215 nm (for L-phenylalanine and L-tyrosine), and 258 nm (for trans-cinnamic acid, p-coumaric acid, styrene). Under these conditions L-phenylalanine, L-tyrosine, p-coumaric acid, trans-cinnamic acid, and styrene were read at 4.5, 6.7, 8.67, 8.78, and 10.4 min respectively.

All gas chromatography (GC) analysis was performed on a Hewlett Packard 5890 Series II gas chromatograph with a flame ionizing detector (FID) and Agilent DB-5 (30 m×0.25 mm ID) fused-silica capillary column using helium as the carrier gas. A GC-FID method was developed to separate and measure styrene concentrations in off gas and headspace samples. In this case, the injector, column, and detector temperatures were set to 180, 150, and 280° C., respectively, and remained constant throughout the method. A GC-FID assay was developed to separate and measure styrene concentrations in n-dodecane solvent samples. In this case, the column temperature began at 60° C. and increased linearly at a rate of 45° C./min until reaching a final temperature of 280° C. The injector and detector temperatures were set to 180 and 280° C., respectively, and remained constant throughout the method.

For all culture experiments, seeds cultures were first grown in Luria Broth (LB) media overnight. Minimal media 1 (herein referred to as "MM1") was used for fermentations which contained glucose (nominally 15 g/L), $MgSO_4.7H_2O$ (0.5 g/L), $NH_4SO_4$ (4.0 g/L), MOPS (24.7 g/L), $KH_2PO_4$ (0.3 g/L), $K_2HPO_4$ (0.7 g/L), and 5 mL/L ATCC Trace Mineral Supplement (EDTA (0.5 g/L), $MgSO_4.7H2O$ (3 g/L), $MnSO_4.7H_2O$ (0.5 g/L), NaCl (1 g/L), $FeSO_4.7H_2O$ (0.1 g/L), $Co(NO_3)_2.6H_2O$ (0.1 g/L), $CaCl_2$ (0.1 g/L), $ZnSO4.7H_2O$ (0.1 g/L), $CuSO_4.5H_2O$ (0.01 g/L), $AlK(SO_4)_2$ (0.01 g/L), $H_3BO_3$ (0.01 g/L), $Na_2MoO_4.2H_2O$ (0.01 g/L), $Na_2SeO_3$ (0.001 g/L), $Na_2WO_4.2H_2O$ (0.10 g/L), and $NiCl_2.6H_2O$ (0.02 g/L)).

Cloning of Candidate Genes Encoding PAL Activity from *A. variabilis*, *N. punctiforme*, *S. maritimus*, and *A. thaliana*

Candidate PAL encoding genes, namely SEQ ID NO:1, SEQ ID NO:2, and SEQ ID NO:3, were amplified via PCR using genomic DNA templates derived from *A. variabilis*, *N. punctiforme*, and *S. maritimus*, respectively. The oligonucleotides primers used to amplify pal from *A. variabilis* (SEQ ID NO:1) are given as SEQ ID NO:12 and SEQ ID NO:13. The oligonucleotides primers used to amplify pal from *N. punctiforme* (SEQ ID NO:2) are given as SEQ ID NO:14 and SEQ ID NO:15. The oligonucleotides primers used to amplify encP from *S. maritimus* (SEQ ID NO:3) are given as SEQ ID NO:16 and SEQ ID NO:17. The oligonucleotides primers used to amplify PAL1 and PAL2 from *A. thaliana* (SEQ ID NO:4 and SEQ ID NO:5, respectively) are given as SEQ ID NO:26 and SEQ ID NO:27 and SEQ ID NO:28 and SEQ ID NO:29, respectively. In all cases, amplified linear DNA fragments were subsequently cleaned using Zyppy Clean and Concentrator kit (Zymo Research, Orange, Calif.). Amplified fragments from *A. variabilis*, *N. punctiforme*, and *S. maritimus* were then treated by restriction endonuclease digestion with the enzymes BamHI and EcoRI while fragments from *A. thaliana* were treated with EcoRI and SphI with appropriate digestion buffer for 3 h at 37° C. Samples of the expression vector pSTV28 were similarly digested with either BamHI and EcoRI or EcoRI and SphI. All digested fragments were subsequently purified using the Zyppy Gel DNA recovery kit (Zymo Research, Orange, Calif.) per manufacturer's instruction. Gene inserts and linearized plasmid DNA were then appropriately ligated together by treatment with T4 DNA ligase (New England Biolabs, Ipswich, Mass.) at 4° C. overnight. Ligase reaction mixtures were then transformed into chemically competent *E. coli* NEB10-Beta. Selection of transformants was achieved by plating transformed cells on LB solid agar media containing 34 mg/L chloramphenicol and culturing overnight at 37° C. Vectors with correct gene insert for all PAL encoding genes were confirmed by mapping the recombinant plasmid by digestion with appropriate restriction enzymes. These cloning works resulted in the successful generation of the plasmids pSpalAv, pSpalNp, pSencPSm, pSpal1At, and pSpal2At.

Cloning of Candidate Genes Encoding CADC Activity from *L. plantarum*, *B. subtilis*, and *S. cerevisiae*

Candidate CADC encoding genes, namely SEQ ID NO:8, SEQ ID NO:9, SEQ ID NO:10, were amplified via PCR using genomic DNA templates derived from *L. plantarum*, *B. subtilis*, and *S. cerevisiae*, respectively. The oligonucleotides primers used to amplify pdc from *L. plantarum* (SEQ ID NO:8) are given as SEQ ID NO:18 and SEQ ID NO:19. The oligonucleotides primers used to amplify padC from *B. subtilis* (SEQ ID NO:9) are given as SEQ ID NO:20 and SEQ ID NO:21. The oligonucleotides primers used to amplify PAD1 from *S. cerevisiae* (SEQ ID NO:10) are given as SEQ ID NO:22 and SEQ ID NO:23. The oligonucleotides primers used to amplify FDC1 from *S. cerevisiae* (SEQ ID NO:11) are given as SEQ ID NO:24 and SEQ ID NO:25. In all cases, amplified DNA fragments were subsequently cleaned using Zyppy Clean and Concentrator kit (Zymo Research, Orange, Calif.). Fragments were then treated by restriction enzyme digestion with appropriate enzymes and buffer for 3 h at 37° C. Amplified fragments of padc and pdc were digested with BamHI and SbfI for which the *E. coli* expression vector pTrc99A was also digested with BamHI and SbfI. Amplified DNA fragments of PAD1 was digested with NcoI and XbaI and DNA fragments of FDC1 were digested with SalI and HindIII. Meanwhile, the *E. coli* expression vector pTrc99A was similarly digested with either NcoI and XbaI for the insertion of PAD1 or with SalI and HindIII for the insertion of FDC1. All digested fragments were subsequently purified using the Zyppy Gel DNA recovery kit (Zymo Research, Orange, Calif.) per manufacturer's instruction. Gene inserts and linearized plasmid DNA were then appropriately ligated together by treatment with T4 DNA ligase (New England Biolabs, Ipswich, Mass.) at 4° C. overnight. Ligase reaction mixtures were then transformed into chemically competent *E. coli* NEB10-Beta. Selection of transformants was achieved by plating transformed cells on LB solid agar media containing 100 mg/L ampicillin and culturing overnight at 37° C. Among the resultant transformants, the vectors with the correct insertion of the genes padC, pdc, and PAD1 were confirmed among clones by digestion with restriction enzyme SphI. Under these conditions, vectors containing the correct gene insert were identified as those which displayed fragments of 2.5 kb and 2 kb (pdc), 2.5 kb, 1.75 kb and 0.25 kb (padc), and 3 kb and 1.8 kb (PAD1) when separated on a 0.7% w./v. agarose gel at 90V for 60 min. The vector with the correct gene insert for FDC1 was confirmed among clones by digestion with restriction enzymes HindIII and NdeI. Under these conditions, vectors containing the correct gene insert were identified as those which displayed fragments of 3.3 kb and 2.4 kb when separated on a 0.7% w./v. agarose gel at 90V for 60 min. These cloning works resulted in the successful generation of the plasmids pTpadCBs, pTpdcLp, pTpad1Sc, and pTfdc1Sc. The newly generated plasmid pTpad1Sc was then digested with SalI and HindIII and cleaned using Zyppy Gel DNA recovery kit (Zymo Research, Orange, Calif.). The SalI and HindIII digested FDC1 fragment was then ligated with pTpad1Sc by treatment with T4 DNA ligase (New England Biolabs, Ipswich, Mass.) at 4° C. overnight. Ligase reaction mixtures were then transformed into chemically competent *E. coli* NEB10-Beta. Transformants were then plated on LB agar containing 100 mg/L ampicillin and incubated at 37° C. overnight. The successfully generated plasmid pTpad1-fdc1 was then confirmed among clones by digestion with restriction enzymes BamHI and HindIII. Under these conditions, vectors containing the correct gene insert were identified as those which displayed fragments of 4.8 kb and 1.6 kb when separated on a 0.7% w./v. agarose gel at 90V for 60 min.

Cloning of Candidate Genes Encoding Styrene Oxygenase Activity from *P. putida* and *R. opacus*

Candidate styrene oxygenase encoding genes, namely SEQ ID NO:6 and SEQ ID NO:7, were amplified via PCR using genomic DNA templates derived from *P. putida* and *R. opacus*, respectively. The oligonucleotides primers used to amplify styAB from *P. putida* (SEQ ID NO:6) are given as SEQ ID NO:30 and SEQ ID NO:31. The oligonucleotides primers used to amplify styA2B from *R. opacus* (SEQ ID NO:7) are given as SEQ ID NO:32 and SEQ ID NO:33. In all cases, amplified DNA fragments were subsequently cleaned using Zyppy Clean and Concentrator kit (Zymo Research, Orange, Calif.). Potential styrene monooxygenases were coexpressed on the plasmid pTfdc1Sc. Fragments and the vector were then treated by restriction enzyme digestion with appropriate enzymes and buffer for 3 h at 37° C. Amplified DNA fragments and pTfdc1Sc of styAB and styA2B were digested with BamHI and XbaI and NcoI and XbaI, respectively. Digested fragments were subsequently cleaned using Zyppy Gel DNA recovery kit (Zymo Research, Orange, Calif.). Gene inserts and linearized plasmid DNA were ligated together by treatment with T4 DNA ligase (New England Biolabs, Ipswich, Mass.) at 4° C. overnight. Ligation mixtures were subsequently transformed into chemically competent *E. coli* NEB10-beta (New England Biolabs, Ipswich, Mass.). Selection of transformants was achieved by plating transformed cells on LB solid agar media containing 100 mg/L ampicillin and culturing overnight at 37° C. Vectors with correct gene insert were then identified and confirmed by mapping the recombinant plasmid by digestion with appropriate restriction enzymes. These works resulted in the generation of plasmids pTfdc1Sc-styABPp and pTfdc1Sc-styA2BRo.

Example 1

Assaying PAL/TAL Activities in Recombinant *E. coli*

*E. coli* BL21(DE3) was individually transformed with each of the plasmids pSpalAv, pSpalNp, pSencPSm, pSpal1At, and pSpal2At. Seeds cultures of each strain were first grown in LB broth supplemented with 34 mg/L chloramphenicol at 30° C. while shaking at 250 rpm overnight. 50 µl of seed culture was then used to inoculate 5 ml of LB broth supplemented with 34 mg/L chloramphenicol. Cultures were grown at 30° C. to an $OD_{600}$ of approximately 0.6. Cultures were then induced by the addition of IPTG to a final concentration of 0.2 mM. Cultures were then allowed to grow for an additional 6 h. Cultures were harvested by first centrifuging for 4 minutes at 1700×g before resuspending the cell pellet in 900 µL distilled water. Cells were then lysed using FastBreak Cell Lysis Reagent kit (Promega, Madison, Wis.) according to manufacturer's specifications and the supernatant collected. PAL activity assays were then performed at room temperature in 50 mM Tris-HCl buffer containing 100 mM L-phenylalanine. The reaction was initiated by the addition of 5 µl of crude cell lysate and followed for 30 min at 20 sec intervals. A molar extinction coefficient of 9,000 $M^{-1}$ $cm^{-1}$ and a 1 cm path length were then used to establish concentration calibrations. The total protein content in each crude lysate was determined using a Bradford protein assay with external standards as a calibration. The enzyme activity was expressed in terms of U $mg^{-1}$ total protein. The obtained results are listed in Table 1.

TABLE 1

Specific activity of PAL isoenzymes from *A. variabilis*, *N. punctiforme*, *S. maritimus* and *A. thaliana* on L-phenylalanine and L-tyrosine when expressed in recombinant *E. coli*.

| *E. coli* Strain | Substrate | Specific Activity (U mg$^{-1}$ total protein) |
| --- | --- | --- |
| BL21 (DE3) | L-phenylalanine | Not detected |
| | L-tyrosine | Not detected |
| BL21 (DE3) pSencPSm | L-phenylalanine | Not detected |
| | L-tyrosine | Not detected |
| BL21 (DE3) pSpalAv | L-phenylalanine | 0.018 ± 0.006 |
| | L-tyrosine | Not detected |
| BL21 (DE3) pSpalNp | L-phenylalanine | 0.006 ± 0.003 |
| | L-tyrosine | Not detected |
| BL21 (DE3) pSpal1At | L-phenylalanine | 0.026 ± 0.010 |
| | L-tyrosine | Not detected |
| BL21 (DE3) pSpal2At | L-phenylalanine | 0.038 ± 0.001 |
| | L-tyrosine | Not detected |

Both PAL and TAL activities were also investigated according to whole cell assays. Seed cultures consisting of 5 ml of LB broth containing 34 mg/L chloramphenicol were prepared of *E. coli* BL21(DE3) strains that were individually transformed with each of pSpalAv, pSpalNp, pSencPSm, pSpal1At, and pSpal2At. These cultures were grown for 12 hours at 30° C. while agitating at 250 rpm. 1 mL of each culture was then used to inoculate 3×250 mL cultures flasks containing 50 mL of LB supplemented with 34 mg/L chloramphenicol. All cultures were then grown at 30° C. while agitating at 250 rpm until an OD$_{600}$ of 0.6 was reached, at which point the cultures were induced by IPTG addition to a final concentration of 0.2 mM. Cultures were then grown for an additional 6 h before the cells were then collected by centrifugation in 50 ml Falcon tubes for 5 min at 1400×g and washed once with pH7 PBS (phosphate buffered saline) buffer. The entire cell pellet was then resuspended in 10 ml pH7 PBS buffer before the appropriate substrate, L-phenylalanine or L-tyrosine, was added at a final concentration of 1 g/L. The results for L-phenylalanine addition are shown in FIG. 2. For all strains tested the addition of L-tyrosine did not result in the formation of p-coumaric acid, indicating that no TAL activity was displayed by these recombinant strains.

These results demonstrate how PAL activity can be attained in recombinant *E. coli* by the expression of pal from either *A. variabilis*, *N. punctiforme*, or *A. thaliana*. Importantly, the selected isoenzymes show high substrate specificity such that no TAL activity was also observed. These results further establish the generation of recombinant *E. coli* strains that are specifically capable of converting phenylalanine to trans-cinnamic acid.

Example 2

Assaying PADC Activities in Recombinant *E. coli*

Seed cultures consisting of 5 ml of LB broth containing 100 mg/L ampicillin were prepared of *E. coli* BL21(DE3) strains that were individually transformed with each of pTpad1-fdc1, pTpad1Sc, pTfdc1Sc, pTpdcLp, and pTpadCBs. These cultures were grown for 12 hours at 30° C. while agitating at 250 rpm. 1 mL of each culture was then used to inoculate 3×250 mL cultures flasks containing 50 mL of LB supplemented with 100 mg/L ampicillin. The culture was then grown at 30° C. while agitating at 250 rpm until it reached an OD$_{600}$ of 0.6, at which point the cultures were induced by the addition of IPTG to a final concentration of 0.2 mM. Cultures were then grown for an additional 6 h. Cells were then collected by centrifuging in 50 ml Falcon tubes for 5 min at 1400×g and washed once with pH7 PBS (phosphate buffered saline) buffer. The entire cell pellet was resuspended in 10 ml pH7 PBS buffer and the appropriate substrate (trans-cinnamic acid or p-coumaric acid) added at a final concentration of 1 g/L. Enzyme activity was monitored by taking 1 mL samples from the culture at both the time of initiation as well as after 12 h of culture. All samples were then analyzed by HPLC using the methods described herein. The results are shown in FIG. 3.

These results demonstrate that PADC candidate isoenzymes from *L. plantarum* and *B. subtilis* display activity on p-coumaric acid alone. Meanwhile, FDC1 from *S. cerevisiae* demonstrates broad substrate specificity with activities on both p-coumaric and trans-cinnamic acid. It is important to note that FDC1 is unique in that only its expression resulted in CADC activity in recombinant *E. coli*. Furthermore, our experiments demonstrate that the expression of FDC1 alone is sufficient for achieving CADC activity in recombinant *E. coli* and is not dependent upon the co-expression of PAD1. Finally, these results also indicate that FDC1 shows a preference for trans-cinnamic acid over p-coumaric acid as substrates since higher product yields can be obtained on the former substrate.

Example 3

PAL and CADC Co-Expression in *E. coli* NST74 to Convert Glucose to Styrene in Shake Flask Cultures The phenylalanine over-producing strain *E. coli* NST74 was co-transformed with the plasmids pSpalAv and pTfdc1Sc resulting in the construction of *E. coli* NST74 pSpalAv pTfdc1Sc. Similarly, *E. coli* NST74 was co-transformed with the following combinations of plasmids: pSpalNp together with pTfdc1Sc, pSpal1At together with pTfdc1Sc, and pSpal2At together with pTfdc1Sc. All strains were selected on LB agar supplemented with 100 mg/L ampicillin and 34 mg/L chloramphenicol and screened for said resistances. These transformations resulted in the generation of *E. coli* NST74 pSpalNp pTfdc1Sc, *E. coli* NST74 pSpal1At pTfdc1Sc, and *E. coli* NST74 pSpal2At pTfdc1Sc. Single colonies of each strain were then selected from the resultant transformants and those strains were grown in 5 mL LB broth supplemented with both 100 mg/L ampicillin and 34 mg/L chloramphenicol. Seed cultures were grown for 12 hours at 32° C. with shaking at 250 rpm. 1 ml of each seed culture was then used to inoculate 50 mL MM1 supplemented with 100 mg/L ampicillin and 34 mg/L chloramphenicol. These cultures were performed in 100 mL serum bottles outfitted with septa caps that were sealed upon inoculation. A closed system was used in this example to avoid volatile product losses. The cells were then cultivated for 10 h at 30° C. with shaking at 250 rpm prior to being induced by the addition of IPTG to a final concentration of 0.2 mM. 1 ml samples were taken from each culture at the time of induction and 29 h post induction and analyzed for metabolite content via HPLC using methods described herein. The strains *E. coli* NST74 pSpalAv pTfdc1Sc, *E. coli* NST74 pSpalNp pTfdc1Sc, *E. coli* NST74 pSpal1At pTfdc1Sc, and *E. coli* NST74 pSpal2At pTfdc1Sc resulted in final styrene titers of 210 mg/L, 185 mg/L, 188 mg/L, and 245 mg/L, respectively.

These results illustrate how a strain of *E. coli* can be constructed to synthesize styrene as a dominant product when supplied with glucose as a sole carbon and energy source. The inventions describes a process in which recombinant *E. coli* has been engineered to co-express enzymes which display both PAL and CADC activities. In the preferred embodiments, the *E. coli* host strain will be a phenylalanine overproducing strain, PAL activity will be encoded by pal from *N. punctiforme*, and CADC activity will be encoded by FDC1 from *S. cerevisiae*.

Example 4

Whole Cell Production of Styrene Upon L-Phenylalanine Supplementation

The phenylalanine over-producing strain *E. coli* NST74 was co-transformed with the plasmids pSpalAt1 and pTfdc1Sc resulting the generation of *E. coli* NST74 pSpalAt1 pTfdc1Sc. This transformation resulted in the generation of *E. coli* NST74 pSpal1At pTfdc1Sc. Strains were selected on LB agar supplemented with 100 mg/L ampicillin and 34 mg/L chloramphenicol and screened for said resistances. Single colonies were then selected from the resultant transformants and were grown in 5 mL LB broth supplemented with both 100 mg/L ampicillin and 34 mg/L chloramphenicol. These seed cultures were grown for 12 hours at 32° C. while shaking at 250 rpm. After which 1 ml of each seed culture was then used to inoculate 50 mL LB supplemented with 100 mg/L ampicillin and 34 mg/L chloramphenicol. Culture were then grown at 30° C. while agitating at 250 rpm until reaching an $OD_{600}$ of 0.6, at which point all cultures were induced by the addition of IPTG to a final concentration of 0.2 mM. Cultures were then incubated for an additional 12 h. Cells were then harvested and collected by centrifugation in 50 ml conical tubes for 5 min at 1400×g and washed once with pH7 PBS (phosphate buffered saline) buffer. The entire cell pellet was resuspended in 10 ml pH7 PBS buffer and the appropriate substrate (L-phenylalanine) added at a final concentration of either 400 or 950 mg/L. After which 1 mL samples from the culture were taken at both the time of initiation as well as periodically over the course of the following 27 h. All samples were then analyzed by HPLC using the methods described herein. The results are shown in FIG. 4.

These results show the ability of *E. coli* NST74 pSpal1At pTfdc1Sc to achieve even higher final styrene titers upon the exogenous supplementation of the cultures with L-phenylalanine. When 400 mg/L of L-phenylalanine was added to the cell suspensions up to 300 mg/L of styrene was produced. Meanwhile, when 950 mg/L of L-phenylalanine was added to the cell suspensions up to 500 mg/L of styrene was produced.

Example 5

Continuous Recovery of Styrene from Cultures by Gas Stripping or Vacuum Extraction Considering the innate volatility of styrene we propose that styrene could be removed from cultures as vapor on either a continuous or discrete basis. Styrene vapor removal could be accomplished either as it is synthesized or shortly thereafter. Styrene vapor removal could be accomplished either by gas stripping by culture aeration or by vacuum application upon the headspace. Styrene vapors could then be collected, for example, by condensation.

Figure 5:
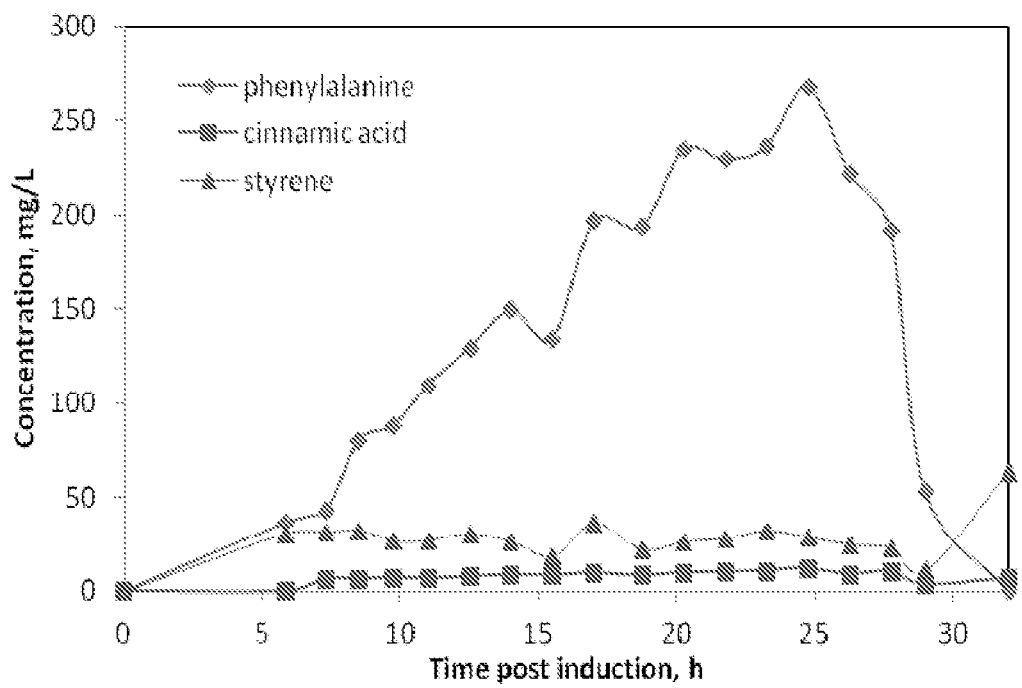
FIG. 5. Concentrations of aromatic metabolites in the aqueous media produced by the strain *E. coli* NST74 pSpal2At pTfdc1Sc when cultivated in a continuously-aerated 1 L bioreactor for 33 hours.
Figure 6:
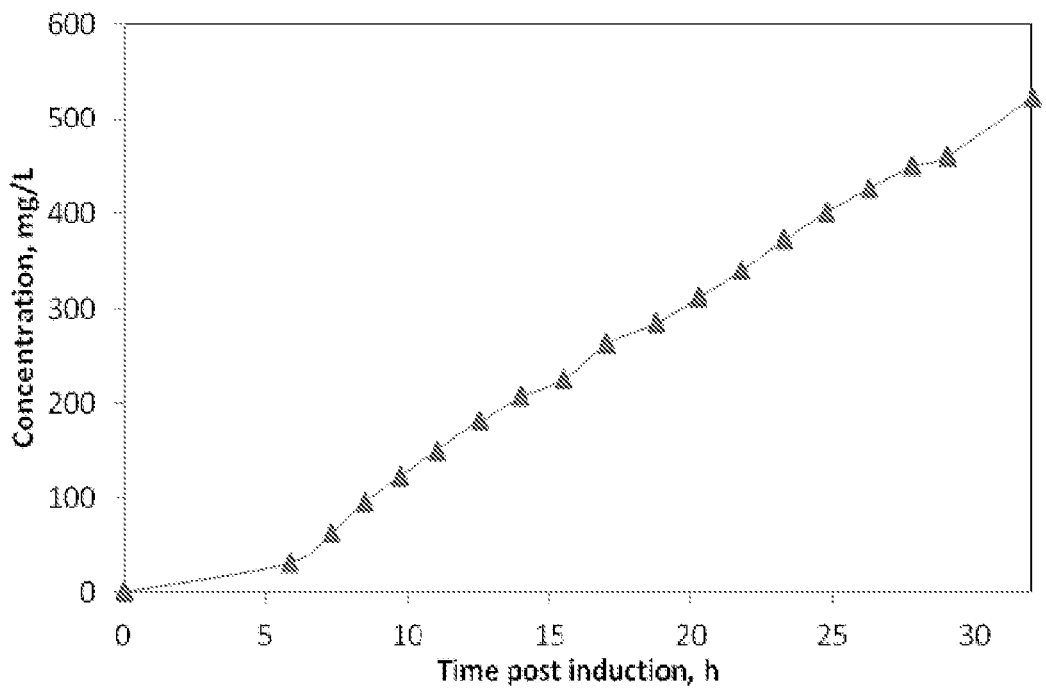
FIG. 6. Net equivalent styrene titer produced by the strain *E. coli* NST74 pSpal2At pTfdc1Sc when cultivated in a continuously-aerated 1 L bioreactor for 33 hours.
Figure 7:
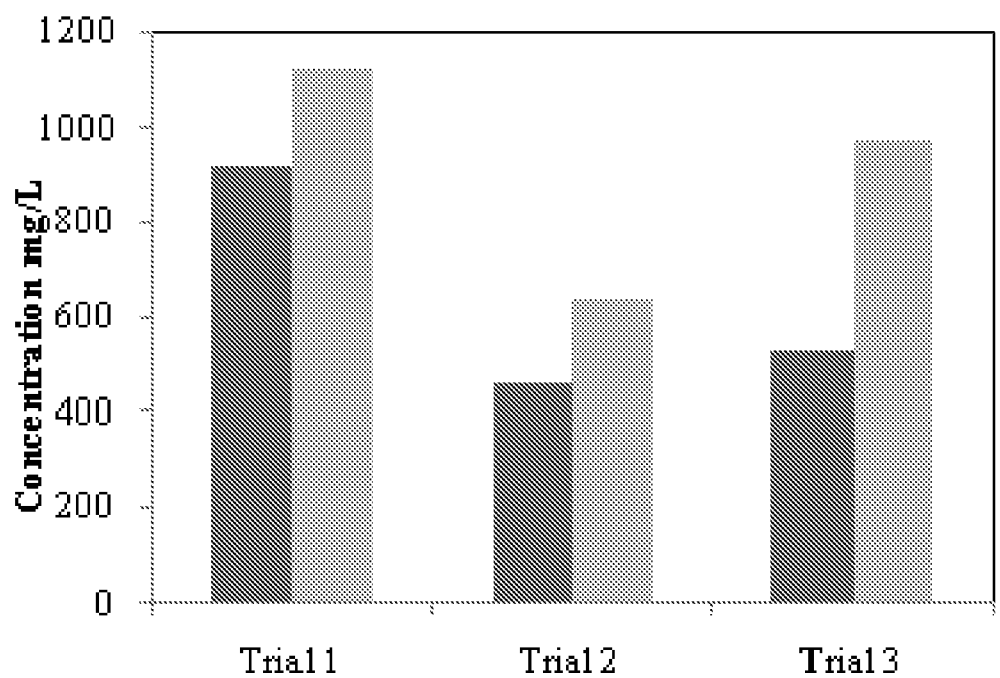
FIG. 7. Styrene oxide production levels after 24 (dark grey) and 48 (light grey) hours after induction of the strain *E. coli* NST74 pSTV28-pal2At pTrc99a-fdc1Sc-styABPp.

The phenylalanine over-producing strain *E. coli* NST74 was co-transformed with the plasmids pSTV28-pal2At and pTrc99A-fdc1Sc resulting in the construction of *E. coli* NST74 pSTV28-pal2At pTrc99A-fdc1Sc. The strain was selected via its ability to survive and grow on LB agar supplemented with 100 mg/L ampicillin and 34 mg/L chloramphenicol. Single colonies were then selected from the resultant transformants and those strains were grown in 5 mL LB broth supplemented with both 100 mg/L ampicillin and 34 mg/L chloramphenicol. These seed cultures were grown for 12 hours at 32° C. with shaking at 250 rpm. After that 1 ml of each seed culture was then used to inoculate 50 mL MM1 supplemented with 100 mg/L ampicillin and 34 mg/L chloramphenicol. These flask cultures were grown for 12 hours at 32° C. with shaking at 250 rpm. Then 20 mL of these flask cultures were then used to inoculate a 2 L bioreactor containing 1 L MM1 supplemented with both 100 mg/L ampicillin and 34 mg/L chloramphenicol. The bioreactor culture was then grown at 30° C. with agitation at 250 rpm and aeration at 0.42 L/min. Upon reaching an $OD_{600}$ of 0.5 the culture was induced by the addition of IPTG to a final concentration of 0.2 mM. The culture was then grown at these conditions for an additional 33 hours. The outlet gas stream was routinely monitored for styrene content by sampling the outlet gas with a 200 μL gas tight syringe and analyzing those samples on the GC-FID. In addition, 1 mL of the aqueous media was also sampled and analyzed by HPLC, and the results are shown in FIG. 5. FIG. 6 shows the net equivalent styrene titer achieved as a function of culture time, accounting for both the styrene stripped from the bioreactor as well as residual amount that remains in the aqueous media. After 33 hours, the net equivalent styrene titer achieved in the bioreactor was equal to 523 mg/L.

Example 6

Continuous Recovery of Styrene from Cultures by Solvent Extraction

The phenylalanine over-producing strain *E. coli* NST74 was co-transformed with the plasmids pSTV28-pal2At and pTrc99A-fdc1Sc resulting in the construction of *E. coli* NST74 pSTV28-pal2At pTrc99A-fdc1Sc. The strain was selected via its ability to survive and grow on LB agar supplemented with 100 mg/L ampicillin and 34 mg/L chloramphenicol. Single colonies were then selected from the resultant transformants and those strains were grown in 5 mL LB broth supplemented with both 100 mg/L ampicillin and 34 mg/L chloramphenicol. These seed cultures were grown for 12 hours at 32° C. with shaking at 250 rpm. After which 1 ml of each seed culture was then used to inoculate 50 mL MM1 supplemented with 100 mg/L ampicillin and 34 mg/L chloramphenicol in a 250 mL baffled flasks. An additional 10 mL of n-dodecane was added to the flask as an insoluble solvent phase. Cultures were then grown for 8 h at 30° C. while shaking at 250 rpm prior to being induced by the addition of IPTG to a final concentration of 0.2 mM. Growth continued at these conditions for the next 48 hours. After 48 hours, the n-dodecane phase was separated from the aqueous media phase by gravity, and 1 mL was analyzed for metabolite content via GC-FID. The styrene concentration in the n-dodecane phase was 2.72 g/L. This level of production would be equivalent to 544 mg/L of styrene produced in the aqueous culture media.

Example 7

Co-Expression of PAL, CADC, and Styrene Monooxygenase Encoding Isoenzymes in *E. coli* NST74 to Convert Glucose to Styrene Oxide in Batch Cultures The phenylalanine over-producing strain *E. coli* NST74 was co-transformed with the plasmids pSTV28-pal2At and pTrc99A-fdc1Sc-styABPp resulting in the construction of *E. coli* NST74 pSTV28-pal2At pTrc99A-fdc1Sc-styABPp. The strain was selected via their ability to survive and grow on LB agar supplemented with 100 mg/L ampicillin and 34 mg/L chloramphenicol. Single colonies were then selected from the resultant transformants and those strains were grown in 5 mL LB broth supplemented with both 100 mg/L ampicillin and 34 mg/L chloramphenicol. These seed cultures were grown for 12 hours at 32° C. with shaking at 250 rpm. 1 ml of each seed culture was then used to inoculate 50 mL MM1 supplemented with 100 mg/L ampicillin and 34 mg/L chloramphenicol. These cultures were grown in 250 mL baffled flasks. The cells were then grown for 8 h at 30° C. with shaking at 250 rpm prior to being induced by the addition of IPTG to a final concentration of 0.2 mM and grown at these conditions for the next 48 hours. 1 ml samples were taken from each culture at intervals of 24 and 48 hours post induction and analyzed for metabolite content via HPLC using methods described herein. FIG. 5 shows the results obtained with the strain NST74 pSTV28-pal2At pTrc99a-fdc1Sc-styABPp for three identical trials run in parallel.

REFERENCES

1. SRI Styrene. Access Intelligence LLC Inc. (2010).
2. DoE. (ed. O.o.E.E.a.R.E.U.S.D.o. Energy) 2002).
3. Fernandez, X. et al. Chemical composition of the essential oils from Turkish and Honduras Styrax. Flavour and Fragrance Journal 20, 70-73 (2005).
4. Qi, W. W. et al. Functional expression of prokaryotic and eukaryotic genes in *Escherichia coli* for conversion of glucose to p-hydroxystyrene. Metabolic engineering 9, 268-276 (2007).
5. Verhoef, S., Wierckx, N., Westerhof, R. G., de Winde, J. H. & Ruijssenaars, H. J. Bioproduction of p-hydroxystyrene from glucose by the solvent-tolerant bacterium *Pseudomonas putida* S12 in a two-phase water-decanol fermentation. Appl Environ Microbiol 75, 931-936 (2009).
6. Wierckx, N. J., Ballerstedt, H., de Bont, J. A. & Wery, J. Engineering of solvent-tolerant *Pseudomonas putida* S12 for bioproduction of phenol from glucose. Appl Environ Microbiol 71, 8221-8227 (2005).
7. Verhoef, S., Ruijssenaars, H. J., de Bont, J. A. & Wery, J. Bioproduction of p-hydroxybenzoate from renewable feedstock by solvent-tolerant *Pseudomonas putida* S12. Journal of biotechnology 132, 49-56 (2007).
8. Hertweck, C. & Moore, B. S. A plant-like biosynthesis of benzoyl-CoA in the marine bacterium '*Streptomyces maritimus*'. Tetrahedron 56, 9115-9120 (2000).
9. Xiang, L. K. & Moore, B. S. Biochemical characterization of a prokaryotic phenylalanine ammonia lyase. Journal of Bacteriology 187, 4286-4289 (2005).
10. Moffitt, M. C. et al. Discovery of two cyanobacterial phenylalanine ammonia lyases: Kinetic and structural characterization. Biochemistry 46, 1004-1012 (2007).
11. Cui, J. D., Jia, S. R. & Sun, A. Y. Influence of amino acids, organic solvents and surfactants for phenylalanine ammonia lyase activity in recombinant *Escherichia coli*. Letters in Applied Microbiology 46, 631-635 (2008).
12. Larsson, S., Nilvebrant, N. O. & Jonsson, L. J. Effect of overexpression of *Saccharomyces cerevisiae* Pad1p on the resistance to phenylacrylic acids and lignocellulose hydrolysates under aerobic and oxygen-limited conditions. Applied Microbiology and Biotechnology 57, 167-174 (2001).
13. Mukai, N., Masaki, K., Fujii, T., Kawamukai, M. & Iefuji, H. PAD1 and FDC1 are essential for the decarboxylation of phenylacrylic acids in *Saccharomyces cerevisiae*. Journal of Bioscience and Bioengineering 109, 564-569 (2010).
14. Panke, S., Wubbolts, M. G., Schmid, A. & Witholt, B. Production of enantiopure styrene oxide by recombinant *Escherichia coli* synthesizing a two-component styrene monooxygenase. Biotechnology and Bioengineering 69, 91-100 (2000).
15. Tischler, D. et al. StyA1 and StyA2B from *Rhodococcus opacus* 1CP: a Multifunctional Styrene Monooxygenase System. Journal of Bacteriology 192, 5220-5227 (2010).
16. Ikeda, M. & Katsumata, R. Metabolic Engineering To Produce Tyrosine or Phenylalanine in a Tryptophan-Producing *Corynebacterium glutamicum* Strain. Appl Environ Microbiol 58, 781-785 (1992).

The invention claimed is:

1. A method for the production of styrene comprising:
   (i) contacting a recombinant *Escherichia* cell with a fermentable carbon substrate, said recombinant cell comprising:
      a) at least one gene encoding a polypeptide having phenylalanine ammonia lyase activity as set forth in SEQ ID NO: 4 or 5, and
      b) at least one gene encoding a polypeptide having trans-cinnamic acid decarboxylase activity as set forth in SEQ ID NO: 11,
   (ii) growing said recombinant cell for a time sufficient to produce styrene; and
   (iii) optionally recovering said styrene.

2. A method for the production of styrene oxide comprising:
   (i) contacting a recombinant *Escherichia* cell with a fermentable carbon substrate, said recombinant cell comprising:
      a) at least one gene encoding a polypeptide having phenylalanine ammonia lyase activity as set forth in SEQ ID NO: 4 or 5,
      b) at least one gene encoding a polypeptide having trans-cinnamic acid decarboxylase activity as set forth in SEQ ID NO: 11, and
      c) at least one gene encoding a polypeptide having styrene monooxygenase activity as set forth in SEQ ID NO: 6; and
   (ii) growing said recombinant cell for a time sufficient to produce styrene oxide.

3. The method according to claim 1 wherein said fermentable carbon source is selected from the group consisting of monosaccharides, oligosaccharides, polysaccharides, glycerol, carbon dioxide, methanol, formaldehyde, formate, amino acids, and carbon-containing amines.

4. The method according to claim 1 wherein said fermentable carbon source is selected from the group consisting of glucose or glycerol.

5. The method according to claim 1 wherein said recombinant *Escherichia* cell is a phenylalanine overproducing strain.

6. The method according to claim 1 wherein said recombinant *Escherichia* cell is a cell isolated from plants selected from the group consisting of soybean, rapeseed, sunflower, cotton, corn, tobacco, alfalfa, wheat, barley, oats, sorghum, rice, broccoli, cauliflower, cabbage, parsnips, melons, carrots, grapes, grass seed crops, sugar beets, sugar cane, beans, peas, rye, flax, hardwood trees, softwood trees, and forage grasses.

7. The method according to claim 1 wherein the gene encoding a polypeptide having phenylalanine ammonia lyase activity is derived from *Arabadopsis thaliana*.

8. The method according to claim 1 wherein the genes encoding polypeptides having trans-cinnamic acid decarboxylase activity are derived from *Saccharomyces cerevisiae*.

9. The method according to claim 2 wherein the gene encoding a polypeptide having styrene oxygenase activity is derived from *Pseudomonas putida*.

10. The method according to claim 1 wherein styrene is optionally recovered from the cultures.

11. The method according to claim 10 wherein styrene recovery is performed on either a discrete or continuous basis.

12. The method according to claim 10 wherein styrene recovery is performed by extraction with a biocompatible organic solvent.

13. The method according to claim 10 wherein styrene recovery is performed by gas stripping via bubbling with air or other gases.

14. The method according to claim 10 wherein styrene recovery is performed by vacuum application upon the head space.

15. The method according to claim 13 wherein styrene vapors are collected via condensation.

16. The method according to claim 14 wherein styrene vapors are collected via condensation.

* * * * *

SEQUENCE LISTING

<160> NUMBER OF SEQ ID NOS: 33

<210> SEQ ID NO 1
<211> LENGTH: 1704
<212> TYPE: DNA
<213> ORGANISM: Anabaena variabilis

<400> SEQUENCE: 1

```
atgaagacac tatctcaagc acaaagcaaa acctcatctc aacaattttc ttttactgga      60
aattcttctg ccaatgtaat tattggtaat cagaaactca caatcaatga tgttgcaagg     120
gtagcgcgta atggcacctt agtgtcttta accaataaca ctgatatttt gcagggtatt     180
caggcatctt gtgattacat taataatgct gttgaatctg gggaaccaat ttatggagtg     240
acatctggtt ttggcggtat ggccaatgtt gccatatccc gtgaacaagc atctgaactc     300
caaaccaact tagtttggtt cctgaaaaca ggtgcaggga acaaattacc cttggcggat     360
gtgcgcgcag ctatgctctt gcgtgcaaac tctcatatgc gcggtgcatc tggcatcaga     420
ttagaactta tcagcgtat ggagattttc cttaacgctg gtgtcacacc atatgtgtat     480
gagtttggtt caattggtgc aagtggtgat ttagtgccac tatcctacat tactggttca     540
```

```
ctgataggct tagatcccag ttttaaggtt gacttcaacg gtaaagaaat ggatgcgcca    600
acagctctac gtcaactgaa tttgtcaccc ttgacattgt tgccgaagga aggcttggcg    660
atgatgaacg gcacttcagt catgacaggt attgcagcaa actgcgtcta cgatactcaa    720
attttaactg cgatcgctat gggcgttcac gctctagata tccaagcttt aaacggaacc    780
aatcaatcat tccatccatt tatccataat tccaaaccac atcctggtca attatgggca    840
gcagatcaga tgatttcttt gttagccaat tcccagttag ttcgtgatga gttagatggt    900
aaacacgatt atcgtgatca cgagttgatt caagatcgtt actcactccg atgccttccc    960
cagtatttgg ggccaatcgt tgatggaatt tcccagattg ccaaacaaat tgaaatcgaa   1020
atcaactcag tcaccgataa cccactaatt gatgttgata accaagctag ctatcatgga   1080
ggaaatttcc tcggacagta cgtgggtatg ggaatggatc acctgcgtta ctatattggg   1140
ttattggcta aacacctaga tgtgcagatt gccctcctcg cctcaccaga gtttagcaat   1200
ggactaccac catctttatt aggcaaccga gaacgtaaag tcaatatggg actcaaaggt   1260
ctgcaaatat gcggtaactc aattatgcca ctgttgacct tctatggaaa ttccatcgcc   1320
gatcgctttc ctacccatgc agaacaattt aatcagaaca tcaacagtca aggatacact   1380
tcagcgactc tagcccgccg ttctgtggat atcttccaga attatgtggc gatcgctctg   1440
atgtttggag tccaagctgt tgacctccgc acatataaaa agactggtca ttacgatgca   1500
cgcgcctgtc tatcacctgc aactgagcgc ttatattcag cagtccgcca cgtagttgga   1560
caaaaaccaa cttcagatcg cccatatatt tggaatgata tgagcaagg actggatgag   1620
catattgccc ggatttctgc tgatatcgct gctggtggtg tgattgtgca agcagttcaa   1680
gatatcttac cctgcttgca ttaa                                          1704

<210> SEQ ID NO 2
<211> LENGTH: 1710
<212> TYPE: DNA
<213> ORGANISM: Nostoc punctiforme

<400> SEQUENCE: 2
atgaatataa catctctaca acagaacata acgcgttctt ggcaaatacc tttcactaat     60
agttcagatt caatcgtaac tgtaggcgat cgcaatctga caatcgacga ggttgtaaat    120
gttgctcgtc atggaacaca ggtgcgctta actgataatg cagatgtcat tcggggtgtt    180
caagcatctt gtgattacat taacaatgca gtcgaaacag cacagccaat ttacggggtg    240
acatctggct ttggcggtat ggcagatgtt gtcatctctc gcgaacaagc agcggaactt    300
cagactaatt taatttggtt tctgaaatcc ggcgcaggaa acaaattatc gttagcagac    360
gtgcgtgcag ctatgctctt acgtgcaaat tcacatttgt atggtgcgtc tggtatacga    420
ctcgaactta ttcagcggat tgaaactttc ctcaacgctg gcgtgacacc ccatgtctat    480
gagtttggct ctatcggtgc tagcggcgat ttggtgccat tatcctacat tactggggca    540
ctaatcggtc tagatcctag ctttacagtt gacttcgacg gtaaagaaat ggatgccgtt    600
acagccttgt ctcgtttggg tttgccaaag ttgcaattgc aaccgaaaga aggtttagca    660
atgatgaatg gcacctcagt catgacaggt attgcagcta actgtgtgta cgatgcgaaa    720
gttttgctcg ctctgacaat gggtgtacac gccttagcca tccaaggttt atacggaacg    780
aatcaatctt tccacccgtt tattcatcag tgcaagccac atcccggtca actatggaca    840
gcagatcaaa tgttttctct gctgaaagat tcatctttag ttcgtgaaga gttggatggt    900
```

```
aaacacgaat accgtggtaa agatctgata caggatcgtt attctctccg ctgtctggca    960
cagttcatag ggccaatcgt tgatggggta tcagagatta ccaagcaaat cgaggtagaa   1020
atgaactcag tcaccgataa cccattgatt gatgtcgaga accaagttag ttatcacggc   1080
ggcaattttc tcggacagta tgtgggtgtg acaatggatc gcctacgtta ttacataggg   1140
ctattggcca aacacatcga tgtgcagatt gcacttcttg tctcgccaga gtttagcaac   1200
ggcttaccac cctctttagt tggtaatagc gatcgcaaag ttaatatggg actcaaaggt   1260
ttgcaaatca gtggaaactc gattatgcca ctgttgagct tctatggaaa ttccctagcc   1320
gatcgctttc ctacccacgc cgagcaattt aatcaaaata ttaacagcca aggctatatt   1380
tccgcaaatt tgacacgtcg ttccgtagac atatttcaga attatatggc gatcgcgttg   1440
atgtttggag ttcaagctgt tgacctccgc acatataaga tgaaaggtca ttatgatgca   1500
cgtacatgcc tctcacccaa tactgtgcag ttatacacag cagtctgcga ggtagttgga   1560
aagccactaa cgtctgtgcg tccatacatt tggaacgaca acgagcaatg tttagatgag   1620
catattgccc ggatttcagc tgatatcgct ggtggtggtt taattgtgca agcagttgag   1680
catattttt cgagcttaaa gtcaacgtaa                                     1710

<210> SEQ ID NO 3
<211> LENGTH: 1572
<212> TYPE: DNA
<213> ORGANISM: Streptomyces maratimus

<400> SEQUENCE: 3
atgaccttcg tcatagagct cgacatgaac gtcacgctcg accaacttga ggacgcggcg     60
cgacagcgca cgcccgtgga gctgtccgca cccgtccgct cccgcgtccg cgcctcgcgc    120
gacgtgttgg tgaagttcgt gcaggacgaa cgtgtcatct acggggtcaa caccagcatg    180
gggggcttcg tcgaccacct cgtcccggtg tcccaggccc ggcagctcca ggagaacctg    240
atcaacgcgg tcgccaccaa cgtggggcg tatctggacg acacgaccgc ccggaccatc    300
atgctgtccc gcatcgtgtc gctggcgcgc gggaactccg cgatcacccc ggcgaatctg    360
gacaagctgg tggccgtact caacgccggg atcgtgccgt gcatcccgga gaagggctct    420
tgggcacca gcggtgaccct cggcccgctg ccgcgatcg ccctggtgtg cgcggggcag    480
tggaaggccc gctacaacgg tcagatcatg cccgggcggc aggccctgtc cgaggccggc    540
gtcgagccga tggagctgag ctacaaggat ggcctggccc tgatcaacgg cacgtcaggc    600
atggtcggcc tgggcaccat ggtcctccag gccgcgcgcc ggctcgtgga ccgctacctg    660
caggtgtccg cgttgtcggt cgagggcctg gcaggcatga cgaaaccgtt cgaccctcgc    720
gtgcacggcg tcaagccgca ccgcgggcag cgtcaggtgg cctcgcggtt gtgggagggg    780
cttgccgact cgcacctggc ggtcaacgaa ctggacaccg agcagaccct ggccggagag    840
atgggcacgg tcgccaaggc cggttcgctg gcgatcgagg acgcctactc catccggtgc    900
acgccgcaga tcctcggtcc cgtggtcgat gtgctggacc ggatcggggc gaccctgcag    960
gacgagctga actcctccaa cgacaacccg atcgtcctgc cggaggaggc ggaggtgttc   1020
cacaacgggc acttccacgg ccagtacgtg gccatggcca tggaccacct gaacatggcc   1080
ctggccaccg tgaccaatct cgccaaccgg cgcgtggacc gcttcctgga caagagcaac   1140
agcaacgggc tgcccgcctt cctgtgccgg aagatccgg gactgcgcct gggcctgatg   1200
ggcggccagt tcatgaccgc gtcgatcacc gcggagaccc gcaccctgac cattccgatg   1260
tcggtgcagt ccctcacgag tacggcggac ttccaggaca tcgtgtcctt cggattcgtc   1320
```

-continued

| | |
|---|---|
| gccgcccgcc gcgcccggga ggtactcacc aacgctgcct acgtggtggc cttcgagctg | 1380 |
| ctgtgcgcct gccaggccgt cgacatccgc ggcgcggaca aactgtcctc cttcacccgc | 1440 |
| ccgctctatg agcgcacccg caagatcgtg ccgttcttcg accgggacga gaccatcacc | 1500 |
| gactacgtcg agaagctggc ggccgacctg atcgcgggcg agcccgtcga cgctgccgtg | 1560 |
| gcggcgcact ga | 1572 |

<210> SEQ ID NO 4
<211> LENGTH: 2178
<212> TYPE: DNA
<213> ORGANISM: Arabidopsis thaliana

<400> SEQUENCE: 4

| | |
|---|---|
| atggagatta cggggcaca caagagcaac ggaggaggag tggacgctat gttatgcggc | 60 |
| ggagacatca agacaaagaa catggtgatc aacgcggagg atcctctcaa ctggggagct | 120 |
| gcagcggagc aaatgaaagg tagccatttg gatgaagtga agagaatggt tgctgagttt | 180 |
| aggaagccag ttgtgaatct tggtggtgag actctgacca ttggacaagt ggctgcgatc | 240 |
| tcaactattg gtaacagtgt gaaggtggag ctatcggaga cagctagagc cggtgtgaat | 300 |
| gctagtagtg attgggttat ggagagtatg aacaaaggca ctgatagtta tggtgttact | 360 |
| actggttttg gtgctacttc tcatcggaga accaaaaacg tgtcgcact tcagaaggaa | 420 |
| cttattagat tccttaacgc cggaatattc ggaagcacga agaaacaag ccacacattg | 480 |
| ccacactccg ccacaagagc cgccatgctt gtacgaatca cactctcct ccaaggattt | 540 |
| tccggtatcc gatttgagat tctcgaagca attaccagtt tcctcaacaa caacatcact | 600 |
| ccatctctcc ccctccgtgg tacaatcacc gcctccggag atctcgttcc tctctcctac | 660 |
| atcgccggac ttctcaccgg tcgtcccaat tccaaagcta ctggtcccaa cggtgaagct | 720 |
| ttaacagcag aggaagcttt caaattagca ggaatcagct ccggattctt tgatctccag | 780 |
| cctaaggaag gtctcgcgct agtcaatggc acggcggttg gatctggaat ggcgtcaatg | 840 |
| gtgttattcg aaacgaatgt gtctctctgtt ttggctgaga ttttgtcggc ggttttcgca | 900 |
| gaggtgatga gtggtaagcc tgagttcacc gatcatctca ctcacagact taaacatcat | 960 |
| cccggtcaaa tcgaagcggc ggcgataatg gagcatatcc tcgacggaag ctcgtacatg | 1020 |
| aaattagctc agaagcttca cgagatggat ccgttacaga aacctaaaca agatcgttac | 1080 |
| gctcttcgta cttctcctca atggttaggt cctcaaatcg aagtgatccg ttacgcaacg | 1140 |
| aaatcgatca gcgtgagat taactccgtc aacgataatc cgttgatcga tgtttcgagg | 1200 |
| aacaaggcga ttcacggtgg taacttccaa ggaacaccaa tcggagtttc aatggataac | 1260 |
| acgagattgg cgatagcagc gattggtaaa ctcatgtttg ctcaattctc agagcttgtg | 1320 |
| aatgatttct acaacaatgg tttaccctcg aatctaaccg cttcgaggaa tccaagtttg | 1380 |
| gattatggat tcaagggagc tgagattgca atggcttctt attgttcaga gcttcaatac | 1440 |
| ttagctaatc ctgtgactag ccatgttcaa tcagcagagc aacataacca agatgtcaac | 1500 |
| tctttgggac taatctcgtc tcgcaaaact tctgaagctg ttgatattct caagcttatg | 1560 |
| tcaacaacgt tcctcgttgc gatttgtcaa gctgtggatt tgagacattt ggaggagaat | 1620 |
| ttgagacaga ctgtgaagaa cactgtctct caagtggcga agaaagttct tactactgga | 1680 |
| gtcaatggtg agcttcatcc ttctcgcttc tgcgaaaagg attactcaa agttgtagac | 1740 |
| cgtgaacaag tctacacata cgcggatgat ccttgtagcg caacgtaccc gttgattcag | 1800 |

```
aagctgagac aagttattgt tgaccatgct ttgatcaatg gtgagagtga aagaatgca      1860 gtgacttcaa tcttccataa gattggagct ttcgaggagg agcttaaggc agtgctaccg      1920
aaagaagtgg aagcagcaag agcagcctac gataacgaaa catcggctat cccgaacagg      1980
atcaaggaat gtaggtcgta tccattgtat agattcgtga gggaagagct tggaacagag      2040
cttttgaccg gagagaaagt gacgtcgcct ggagaagagt tcgacaaggt tttcacggcg      2100
atttgtgaag gtaaaatcat tgatccgatg atggaatgtc tcaacgagtg aacggagct      2160 cccattccaa tatgttaa                                                   2178

<210> SEQ ID NO 5
<211> LENGTH: 2154
<212> TYPE: DNA
<213> ORGANISM: Arabidopsis thaliana

<400> SEQUENCE: 5
atggatcaaa tcgaagcaat gttgtgcggc ggaggagaga agacaaaagt ggcggttact        60
acgaagactt tggcagatcc attgaattgg ggtttagcag cggatcaaat gaaaggaagt       120
catttagatg aagtgaagaa gatggtcgaa gagtatcgta gaccagtcgt gaatcttggc       180
ggagaaacac tgacgatcgg acaagttgct gccatctcca ccgtagggag cagcgttaag       240
gttgagttag cggagacttc aagagccggt gtgaaagcta gcagtgattg ggttatggag       300
agcatgaaca aaggtactga cagttacgga gtcaccaccg gctttggtgc tacttctcac       360
cggagaacca aaaacggcac cgcattacaa acagaactca ttagatttt gaacgccgga       420 atattcggaa acacgaagga gacatgtcac acactgccgc aatccgccac aagagccgcc       480
atgctcgtca gagtcaacac tcttctccaa ggatactccg ggatccgatt cgagatcctc       540
gaagcgatta caagtctcct caaccacaac atctctccgt cactacctct ccgtggaacc       600
attaccgcct ccggcgatct cgttcctctc tcttacatcg ccggacttct caccggccgt       660
cctaattcca aagccaccgg tcccgacggt gaatcgctaa ccgcgaaaga agcttttgag       720
aaagccggaa tcagtactgg attcttcgat ttacaaccta aggaaggttt agctctcgtt       780
aatggcacgg cggttggatc tggaatggcg tcgatggttc tattcgaagc gaatgtccaa       840
gcggtgttag cggaggtttt atcagcgatc ttcgcggagg ttatgagcgg gaaacctgag       900
tttaccgatc atctgactca tcgtttaaaa catcatcccg gacaaatcga agcggcggcg       960
ataatggagc acatactcga cggaagctca tacatgaaat tagctcaaaa ggttcacgag      1020
atggatccat tgcagaaacc aaaacaagat cgttacgctc ttcgtacatc tcctcaatgg      1080
ctaggtcctc aaattgaagt aatccgtcaa gctacgaaat cgatagagcg tgaaatcaac      1140
tccgttaacg ataatccgtt gatcgatgtt tcgaggaaca aggcgattca cggtggtaac      1200
ttccaaggaa caccaatcgg agtttctatg gataacacga gattggcgat gctgcgatt      1260 gggaagctaa tgtttgctca attctctgag cttgttaatg atttctacaa caatggactt      1320
ccttcgaatc taactgcttc gagtaatcca agtttggatt atggattcaa aggagcagag      1380
attgctatgg cttcttattg ttctgagctt caatacttgg ctaatccagt cacaagccat      1440
gttcaatcag ctgagcaaca taatcaagat gtgaactctc ttggtttgat ctcgtctcgt      1500
aaaacatctg aagctgtgga tattcttaag ctaatgtcaa caacgttcct tgtggggata      1560
tgtcaagctg ttgatttgag acatttggag gagaatctga acaaactgt gaagaacaca      1620 gtttctcaag ttgctaagaa agtgttaacc actggaatca acggtgagtt acatccgtca      1680
aggttttgcg agaaggactt gcttaaggtt gttgatcgtg agcaagtgtt cacgtatgtg      1740
```

| | |
|---|---|
| gatgatcctt gtagcgctac gtacccgttg atgcagagac taagacaagt tattgttgat | 1800 |
| cacgctttgt ccaacggtga gactgagaag aatgcagtga cttcgatctt tcaaaagatt | 1860 |
| ggagcttttg aagaggagct taaggctgtg cttccaaagg aagttgaagc ggctagagcg | 1920 |
| gcttatggga atggaactgc gccgattcct aaccggatta aggaatgtag gtcgtatccg | 1980 |
| ttgtataggt tcgtgaggga agagcttgga acgaagttgt tgactggaga aaaggttgtg | 2040 |
| tctccgggag aggagtttga taaggtcttc actgctatgt gtgaaggtaa acttattgat | 2100 |
| ccgttgatgg attgtctcaa ggaatggaac ggagctccga ttccgatttg ctaa | 2154 |

<210> SEQ ID NO 6
<211> LENGTH: 1815
<212> TYPE: DNA
<213> ORGANISM: Pseudomonas putida

<400> SEQUENCE: 6

| | |
|---|---|
| atgaaaaagc gtatcggtat tgttggtgca ggcactgccg gcctccatct tggcctcttc | 60 |
| ctccgtcagc atgacgtcga cgtcaccgtg tacacggatc gcaagcccga tgagtacagc | 120 |
| ggacagcgtc tcctgaatac cgttgctcac aacgcggtga cggtgcagcg ggaggttgcc | 180 |
| ctcgacgtca atgagtggcc gtctgaggag tttggctatt cggccacta ctactacgta | 240 |
| ggtgggccgc agcccatgcg ttttctacggt gatctcaagg ctcccagccg tgcagtggac | 300 |
| taccgtctct acctgccgat gctgatgcgt gcactggaag ccaggggcgg caagttctgc | 360 |
| tacgacgccg tgtctgccga agatctggga gggctgtcgg agcagtatga tctgctggtt | 420 |
| gtgtgcactg gtaaatacgc cctcggcaag gtgttcgtga agcagtccga aaactcgccc | 480 |
| ttcgagaagc cgcaacgggc actgtgcgtt ggtctcttca agggcatcaa ggaagcaccg | 540 |
| attcgcgcgg tgactatgtc cttctcgcca gggcatggcg agctgattga gattccaacc | 600 |
| ctgtcgttca atggcatgag cacagcgctg gtgctcgaaa accatattgg tagcgatctg | 660 |
| gaagtcctcg cccacaccaa gtatgacgat gacccgcgtg cgttcctcga tctgatgctg | 720 |
| gagaagctgc gtaagcatca tccttccgtt gccgagcgca tcgatccggc tgagttcgac | 780 |
| ctggccaaca gttctctgga catcctccag ggcggtgttg tgccagtatt ccgcgacggt | 840 |
| catgcgaccc tcaataacgg caaaaccatc atcgggctgg gcgacatcca ggcaactgtc | 900 |
| gatccggtct tggaccaggg cgcgaacatg gcgtcctatg cggcatggat tctgggcgag | 960 |
| gaaatccttg cgcactctgt ctacgacctg cgcttcagcg aacacctgga gcgtcgccgc | 1020 |
| caggatcgcg tgctgtgcgc cacccgctgg accaacttca ctctgagcgc ttcacggaa | 1080 |
| cttccgccgg aattcctcac cttccttcag atcctgagcc agagccgtga atggctgat | 1140 |
| gagttcacgg acaacttcaa ctacccggaa cgtcagtggg atcgcttctc cagcccggaa | 1200 |
| cgtatcggtc agtggtgcag ccagtacgca cccactattg cggcctgacg ctattgctcc | 1260 |
| gctggtcaag gccagcggag ccctaactcc tgggtgattc aaatgacgtt aaaaaagat | 1320 |
| gtggtggtgg atatcgactc caccagcttc cgccaggcgg ttgcactgtt cgcgacggga | 1380 |
| attgcggttc tcagcgcgga gactgacgag ggcgaagtgc atggcatgac ggtgaacagc | 1440 |
| ttcacctcca tcagtctgga cccgccgact gtgatggtgt ccctgaagtc gggccgtatg | 1500 |
| catgagctgc tgactcaagg cggacgcttc ggcgtcagcc tcctgggtga agtcagaag | 1560 |
| atgttatcgg cattcttcag caagcgtgtg atcgatggca ctcctcctcc tgctttcaca | 1620 |
| gctcaggccg gcctccccac tctgcgggac gccatggcct ggttcgaatg cgaggtggag | 1680 |

```
agcacggttg aagtacacga ccacacgctc ttcattgcgc gcgttagcgc ctgtggagtg    1740
ccggaggcga atgccccca gccgctgctg ttctttgcca gccgttatca cggcaacccg     1800
ttgccactga attga                                                     1815

<210> SEQ ID NO 7
<211> LENGTH: 1722
<212> TYPE: DNA
<213> ORGANISM: Rhodococcus opacus

<400> SEQUENCE: 7
atgcgcagca tcgctatcgt cggagccgga caatccgggg cactactggc cctggcctta     60
ctcaagcgtg acttccaggt caccctggcg accgaccgta caccggagga agttcgggtc    120
ggacccgtca tgtcgagcca gtgcatgttc gactcggcac tgcagatcga acgggacctc    180
gggctcgacc gctgggagga gcagtgcccg cgcatcgaca cgatggcggt caacgtggcg    240
aaaacgcacg gcagcaacga atcacggtg tcgaccccgc tggtcggatt cgcgcaatcg     300
gtcgatcagc gagtcaaatg cgcggactgg gtcgacgagt tcgcagcact cggcggcaat    360
ctgatcatca agacagcggg tcccgcggac atcgacgcac tcgcccagag ccacgacctg    420
gtcatcatct ccagcggcaa gggcgacctc ggcagactct ctccccgga tccgctgaaa     480 tcgccctaca accgaccgca gcgcgccctg gcgctggcct acgtgaacgg tctcgcgccg    540 cacccgacg gcgcggacct ctcgctgaac atcgttccgg gagtcggcga gtacttcgtc      600
ctcccggcgc tgaccaccac cgggccctgc cacgtgatgg tcttcgaagg catccccggt    660
ggaccgatgg actgctggga cgatgtccac acaccacacg aacacctcaa ccgcgccaga    720
gaggtactgg ccgagcactt tcccgcggag ttcgccagga ccgccgacat caccccgacc    780
gatgacgccg gggtcctcct cggccggctg acaccgacgg tccgccgacc gtggccgag    840 ctcgcctcgg gcgggtcgt attgggtatg ccgacgcgg tggtcctcaa cgatccactc     900
accgggcaag gcagcaacaa cgcagcccaa gccgccgccg tgtacctcga ggcgatcgtg    960
gaccggggtg accggccgtt cgacgcgcag tggatgcaac gcaccttcga caaattctgg    1020
cgcggatggg ctcagtgggc cgtgtcgtgg accaacgaca tgctccgggg accatccgac    1080
actgtgctcg gactgtttgc ggctgcgcag gactcgccga ccctggcgtc cgcaatcgca    1140 accgattcg atgatccccg caccgtccac aactggtggt cgacgacgc cgaggcgcag     1200 cgtgtgatcg agaacgcacg ggccgccgag caggcccagt cgacccccg tgatctacgg    1260 cgcgcgctcg gccagtacgc cacaggcgtc acggtgatca ctgcgcgggc cccagatggt    1320
cggaagatcg gtgtcacagc gaactcgttc acctcggtgt cgatggatcc gccgctcgtg    1380
tcgtggtgcc cggcgagtaa ggcgccgagc ctccccgacc tcacggcggc cactcatttc    1440
gccgtcaacg tcctggcggc caaccaacac gacctgtccc ggcaattctc gacgccggcc    1500
gaggacaagt tcgcgggtgt ggcgaccacc gagggcattg ccggcgttcc gctgatcgat    1560
gacgccatcg cgcatttcca gtgccggacg gtccaacgag tagaggccgg cgaccacatc    1620
atcttcctcg gcgagatcga agaatatgat gcggaccccg gcgaaccgct ggtcttccac    1680
tcggggtcgt accgcctggt gaccaagcat cccgacttct ga                       1722

<210> SEQ ID NO 8
<211> LENGTH: 537
<212> TYPE: DNA
<213> ORGANISM: Lactobacillus plantarum

<400> SEQUENCE: 8
```

```
atgacaaaaa cttttaaaac acttgatgac tttctcggca cacactttat ctacacttat    60
gataacggct gggaatacga gtggtacgcc aagaacgacc acaccgttga ttaccgaatc   120
cacggtggga tggttgccgg tcgttgggtc actgatcaaa aagctgacat cgtcatgttg   180
accgaaggca tttacaaaat ttcttggact gaaccaactg ggactgacgt tgcactagac   240
ttcatgccca atgagaagaa actacacggt acgattttct tcccaaagtg ggttgaagaa   300
caccctgaaa ttacggtcac ttaccaaaac gaacacatcg atttaatgga acagtctcgt   360
gaaaagtatg ccacttatcc aaaactagtt gtacccgaat tgccaatat  tacttacatg   420 ggcgacgccg gccaaaacaa cgaagatgta atcagtgaag caccttacaa agaaatgccg   480
aatgatattc gcaacggcaa gtactttgat caaaactacc atcgtttaaa taagtaa      537

<210> SEQ ID NO 9
<211> LENGTH: 486
<212> TYPE: DNA
<213> ORGANISM: Lactobacillus plantarum

<400> SEQUENCE: 9
atggaaaact ttatcggaag ccacatgatt tatacgtatg aaaacggatg ggaatacgag    60
atttatatta aaaacgacca tacaattgat tatagaattc atagcggaat ggttgccgga   120
cgctgggttc gagatcagga agtgaatatt gtcaaactga cagaaggcgt atataaagtg   180
tcttggacag agccgactgg cacggatgtt tcattaaact ttatgccaaa tgaaaaacgc   240
atgcatggca ttatttttctt cccgaaatgg gtgcatgaac atcctgaaat tacggtttgc   300
taccaaaatg accacattga tttgatgaaa gaatcccgcg aaaatatga  aacgtatcca   360 aaatacgttg tacctgaatt tgcggaaatt acatttctga aaaatgaagg agtcgacaac   420
gaagaagtga tttcgaaggc tccttatgag ggaatgacag acgatattcg cgcgggaaga   480
ttataa                                                              486

<210> SEQ ID NO 10
<211> LENGTH: 726
<212> TYPE: DNA
<213> ORGANISM: Saccharomyces cerevisiae

<400> SEQUENCE: 10
atgctcctat ttccaagaag aactaatata gccttttca  aaacaacagg cattttttgct    60 aattttcctt tgctaggtag aaccattaca acttcaccat ctttccttac acataaactg   120
tcaaaggaag taaccagggc atcaacttcg cctccaagac caaagagaat tgttgtcgca   180
attactggtg cgactggtgt tgcactggga atcagacttc tacaagtgct aaaagagttg   240
agcgtagaaa cccatttggt gatttcaaaa tggggtgcag caacaatgaa atatgaaaca   300
gattgggaac cgcatgacgt ggcggccttg gcaaccaaga catactctgt tcgtgatgtt   360
tctgcatgca tttcgtccgg atcttttccag catgatggta tgattgttgt gccctgttcc   420
atgaaatcac tagctgctat tagaatcggt tttacagagg atttaattac aagagctgcc   480
gatgtttcga ttaaagagaa tcgtaagtta ctactggtta ctcgggaaac ccctttatct   540
tccatccatc ttgaaaacat gttgtcttta tgcagggcag gtgttataat ttttcctccg   600
gtacctgcgt tttatacaag acccaagagc cttcatgacc tattagaaca aagtgttggc   660
aggatcctag actgctttgg catccacgct gacactttc  ctcgttggga aggaataaaa   720
agcaag                                                              726
```

<210> SEQ ID NO 11
<211> LENGTH: 1512
<212> TYPE: DNA
<213> ORGANISM: Saccharomyces cerevisiae

<400> SEQUENCE: 11

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga agtaaggga aaggagat       240
catggtagaa ttgcccatca tctggggctc gacccaaaaa aactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct gggtgagtc ggttccagta gtaaatgtg agaccaacga tttaatggtt       780
cctgcaacga gtgagatggt atttgagggt actttgtcct aacagatac acatctggaa      840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa aagttggttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                         1512
```

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12

```
taagaattca gggataaaa taatgaagac actatctcaa gc                          42
```

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
attggatcct taatgcaagc agggt                                      25

<210> SEQ ID NO 14
<211> LENGTH: 44
<212> TYPE: DNA
<213> ORGANISM: Artificial Sequence
<220> FEATURE:
<223> OTHER INFORMATION: Primer

<400> SEQUENCE: 14
taagaattca agggataaa taatgaatat aacatctcta caac                  44

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
attggatcct tacgttgact ttaagct                                    27

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
taagaattca agggataaa taatgacctt cgtcatagag ct                    42

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
attggatcct tagtgcgccg ccacg                                      25

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
ataggatccc tctggaggca gttctaatga caaaaacttt taaaacact             49

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
atacctgcag gccagaatgt ttcacgtgaa                                 30

<210> SEQ ID NO 20

```
<211> LENGTH: 47
<212> TYPE: DNA
<213> ORGANISM: Artificial Sequence
<220> FEATURE:
<223> OTHER INFORMATION: Primer

<400> SEQUENCE: 20
aaaggatccc gactaaggga ggataagatg gaaaacttta tcggaag        47

<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
atacctgcag gatgtttatt ataatcttcc cgcg                      34

<210> SEQ ID NO 22
<211> LENGTH: 48
<212> TYPE: DNA
<213> ORGANISM: Artificial Sequence
<220> FEATURE:
<223> OTHER INFORMATION: Primer

<400> SEQUENCE: 22
ttaccatgga ggaacctagg cacacaatgg tcctatttcc aagaagaa       48

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23
atttctagat tacttgcttt ttattccttc cc                        32

<210> SEQ ID NO 24
<211> LENGTH: 49
<212> TYPE: DNA
<213> ORGANISM: Artificial Sequence
<220> FEATURE:
<223> OTHER INFORMATION: Primer

<400> SEQUENCE: 24
atagtcgaca gacatcaaag gacggttcat gaggaagcta aatccagct      49

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
attaagcttt tatttatatc cgtacctttt ccaat                     35

<210> SEQ ID NO 26
<211> LENGTH: 41
<212> TYPE: DNA
<213> ORGANISM: Artificial Sequence
<220> FEATURE:
<223> OTHER INFORMATION: Primer

<400> SEQUENCE: 26
```

-continued taagaattca agggagataaa taatggagat taacgggca c    41

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27
attgcatgct taacatattg gaatgggagc tc    32

<210> SEQ ID NO 28
<211> LENGTH: 43
<212> TYPE: DNA
<213> ORGANISM: Artificial Sequence
<220> FEATURE:
<223> OTHER INFORMATION: Primer

<400> SEQUENCE: 28
taagaattca agggagataaa taatggatca aatcgaagca atg    43

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
attgcatgct tagcaaatcg gaatcggag    29

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
ataggatcca ggaggaagcc atgaaaaagc gtatcggtat tg    42

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31
atatctagag caatcaattc agtggcaacg g    31

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
ataccatgga ggaggcagtc atgcgcagca tcgcta    36

<210> SEQ ID NO 33
<211> LENGTH: 30
<212> TYPE: DNA

```
<213> ORGANISM: Artificial Sequence
<220> FEATURE:
<223> OTHER INFORMATION: Primer

<400> SEQUENCE: 33
atatctagag cggcagaagt cgggatgctt                                      30
```